(12) United States Patent
Barberousse et al.

(10) Patent No.: US 8,148,407 B2
(45) Date of Patent: Apr. 3, 2012

(54) COMPOUNDS DERIVED FROM 5-THIOXYLOSE AND THEIR USE IN THERAPEUTICS

(75) Inventors: Véronique Barberousse, Hauteville les Dijon (FR); Michel Bondoux, Fontaine les Dijon (FR); Didier Thomas, Saint Apollinaire (FR); Vincent Peyrou, Hauteville les Dijon (FR)

(73) Assignee: Laboratories Fournier S.A., Dijon Cedex (FR)

( * ) Notice: Subject to any disclaimer, the term of this patent is extended or adjusted under 35 U.S.C. 154(b) by 928 days.

(21) Appl. No.: 11/909,489

(22) PCT Filed: Mar. 24, 2006

(86) PCT No.: PCT/FR2006/050259
§ 371 (c)(1),
(2), (4) Date: Jun. 19, 2008

(87) PCT Pub. No.: WO2006/100413
PCT Pub. Date: Sep. 28, 2006

(65) Prior Publication Data
US 2008/0293768 A1    Nov. 27, 2008

(30) Foreign Application Priority Data
Mar. 25, 2005 (FR) ..................................... 05 02978

(51) Int. Cl.
*A61K 31/4436* (2006.01)
*C07D 409/12* (2006.01)
(52) U.S. Cl. ..................................... 514/336; 546/280.1
(58) Field of Classification Search .................. 514/336; 546/280.1
See application file for complete search history.

(56) References Cited

U.S. PATENT DOCUMENTS

| | | | |
|---|---|---|---|
| 4,877,808 | A | 10/1989 | Samreth et al. |
| 4,996,347 | A | 2/1991 | Samreth et al. |
| 5,100,913 | A | 3/1992 | Samreth et al. |
| 5,101,048 | A | 3/1992 | Bajgrowicz et al. |
| 5,246,961 | A | 9/1993 | Samreth et al. |
| 2007/0054955 | A1 | 3/2007 | Barberousse et al. |

FOREIGN PATENT DOCUMENTS

| | | |
|---|---|---|
| EP | 0 290 321 A1 | 11/1988 |
| EP | 0 365 397 A2 | 4/1990 |
| EP | 0 367 671 A2 | 5/1990 |
| EP | 0 451 007 A1 | 10/1991 |
| FR | 2 860 234 A1 | 4/2005 |

OTHER PUBLICATIONS

King, Med. Chem. Principle and Practice (1994), pp. 206-208).*
Francois Bellamy, et al., "Thuoxyloside Derivatives As Orally Active Venous Antithrombotics", European Journal of Medicinal Chemistry, Editions Scientifique Elsevier, Paris, France, vol. 30, 1995, pp. 101S-115S, (XP002042895).
International Search Report (PCT/ISA/210) and PCT/ISA/237 (Thirteen (13) pages).
Esko et al., Glycoside Primers and Inhibitors of Glycosylation, Carbohydrate-Based Drug Discovery, vol. 2, 2003, pp. 883-898.
Esko et al., Xyloside Priming of Glycosaminoglycan Biosynthesis and Inhibition of Proteoglycan Assembly, Methods in Molecular Biology, vol. 171: Proteoglycan Protocols, 2001, pp. 317-323.
Esko et al., Unusual β-D-xylosides That Prime Glycosaminoglycans in Animal Cells, The Journal of Biological Chemistry, vol. 271, No. 32, 1996, pp. 19150-19165.
Esko et al., Amino Acid Determinants That Drive Heparan Sulfate Assembly in a Proteoglycan, The Journal of Biological Chemistry, vol. 269, No. 30, 1994, pp. 19295-19299.
Silverman, The Organic Chemistry of Drug Design and Drug Action, 2004, pp. 29-32.

* cited by examiner

*Primary Examiner* — Taofiq A Solola
(74) *Attorney, Agent, or Firm* — Crowell & Moring LLP

(57) ABSTRACT

The invention relates to novel 5-thioxylose compounds, preferably derivatives of the 5-thioxylopyranose type, to the process for their preparation and to their use as active principles of drugs intended especially for the treatment or prevention of thrombosis or cardiac insufficiency.

10 Claims, No Drawings

COMPOUNDS DERIVED FROM 5-THIOXYLOSE AND THEIR USE IN THERAPEUTICS

The present invention relates to novel 5-thioxylose compounds, preferably derivatives of the 5-thioxylopyranose type, to the process for their preparation and to their use as active substances of drugs intended especially for the treatment or prevention of thrombosis.

PRIOR ART

D-xylose derivatives have already been disclosed, e.g. in EP 051 023 B1, U.S. Pat. No. 4,877,808, EP 421 829 B1 or the publication J. Med. Chem., vol. 36 no. 7, pp 898-903. The compounds described in these documents are useful for reducing the risks of venous thrombosis in humans. The mechanism of action of these compounds seems to be an effect on the plasma glycosaminoglycans (J. Biol. Chem., vol. 270 no. 6, pp 2662-68; Thromb. Haemost., 1999, 81, pp 945-950).

SUBJECT OF THE INVENTION

A novel family of compounds derived from thioxylose have now been discovered which exhibit a good antithrombotic activity and can be synthesized efficiently.

DESCRIPTION

The novel compounds according to the invention are selected from:
a) the compounds of the formula

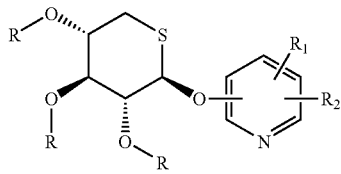

I in which:
  the pentapyranosyl group is a free or acylated 5-thio-β-D-xylopyranosyl group,
  R is a hydrogen atom or a $C_2$-$C_6$ acyl group,
  $R_1$ is a $C_1$-$C_4$ alkylsulfonyl group, a $C_2$-$C_6$ acyl group, a group CONR'R" or a group

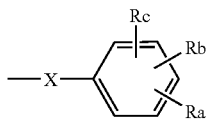

in which:
  X is a single bond, an oxygen atom, a sulfoxy group, a group —CO— or a group —CHOH—,
  Ra is a hydrogen atom, a halogen, a hydroxyl group, a $C_1$-$C_4$ alkyl group, a trifluoromethyl group, a trifluoromethoxy group, a cyano group, a $C_1$-$C_4$ hydroxyalkyl group, a $C_2$-$C_4$ acyl group, a $C_1$-$C_4$ alkoxy group or a group NR'R",
  Rb and Rc independently of one another are each a hydrogen atom, a halogen atom, a $C_1$-$C_4$ alkyl group, a cyano group or a $C_1$-$C_4$ alkoxy group,
  $R_2$ is a hydrogen atom, a $C_1$-$C_4$ alkyl group or a halogen atom, and
  R' and R'" independently are each a hydrogen atom or a $C_1$-$C_4$ alkyl group optionally substituted by an aromatic ring, or form, together with the nitrogen atom to which they are attached, a ring having 5 or 6 carbon atoms;
b) their addition salts; and
c) their active metabolites.

The invention further relates to the compounds of formula I for their use as pharmacologically active substances.

In particular, the invention relates to the use of at least one substance selected from the compounds of formula I and their non-toxic salts for the preparation of a drug that is useful in human or animal therapeutics and is intended for the prevention or treatment of thrombosis, especially venous thrombosis. As the compounds according to the invention are active by a mode of action involving glycosaminoglycans, they may be useful as active substances of a drug intended for the treatment or prevention of any other disease in which glycosaminoglycans are involved.

DETAILED DESCRIPTION

In formula I, $C_1$-$C_4$ alkyl group is understood as meaning a linear, branched or cyclic hydrocarbon chain having from 1 to 4 carbon atoms. Particular examples of $C_1$-$C_4$ alkyl groups are methyl, ethyl, propyl, butyl, 1-methylethyl, 1,1-dimethylethyl, 1-methylpropyl, 2-methylpropyl, cyclopropyl or cyclopropylmethyl groups.

Alkyl group optionally substituted by an aromatic ring is understood as meaning e.g. a phenylmethyl (benzyl) or phenylethyl group.

Halogen is understood as meaning a fluorine, chlorine, bromine or iodine atom, preferably a fluorine or chlorine atom.

$C_2$-$C_6$ acyl group denotes an acetyl, propanoyl, butanoyl, pentanoyl or hexanoyl group or their homologs in which the chain can be branched.

$C_1$-$C_4$ alkoxy group is understood as meaning a linear, branched or cyclic hydrocarbon chain having from 1 to 4 carbon atoms and bonded via an oxygen atom. Examples of $C_1$-$C_4$ alkoxy groups which may be mentioned are methoxy, ethoxy, propoxy, butoxy, 1-methylethoxy, 1,1-dimethylethoxy, 1-methylpropoxy, 2-methylpropoxy or cyclopropylmethoxy groups.

Addition salts are understood as meaning the addition salts obtained by reacting a compound of formula I with a mineral or organic acid. The pharmaceutically acceptable addition salts are preferred. The hydrates or solvates of the compounds of formula I or of the salts of the compounds of formula I also form an integral part of the invention.

Hydrochloric, hydrobromic, phosphoric and sulfuric acids are preferred among the mineral acids suitable for salifying a basic compound of formula I. Methanesulfonic, benzenesulfonic, toluenesulfonic, maleic, fumaric, oxalic, citric, tartaric, lactic and trifluoroacetic acids are preferred among the organic acids suitable for salifying a basic compound of formula I.

Active metabolites are understood as meaning the compounds which are produced in the biological medium from the compounds of formula I and which possess a pharmacological activity of the same nature as that of the compounds of formula I described in the present patent application. For example, the compounds of formula I in which $R_1$ is an acyl group can metabolize by reduction of the ketone group to an alcohol group (—CHOH—) to give a novel compound (metabolite) which retains a pharmacological activity of the same nature as that of the compounds of formula I.

Very particularly preferred compounds according to the present invention are those in which $R_1$ is a phenyl group optionally substituted by the groups Ra, Rb and Rc as defined above.

Other preferred compounds according to the present invention are those in which R is the hydrogen atom or the group —COCH$_3$.

The compounds of formula I according to the invention can be prepared using the glycosylation methods known to those skilled in the art, especially:

a) HELFERICH's method described in the book "The Carbohydrate, Chemistry and Biochemistry", 2nd edition, Academic Press, New York, London 1972, volume IA, pages 292-294, by condensing a peracetylated sugar with a hydroxylated aromatic heterocycle in the presence of a Lewis acid;

b) KOENIGS-KNORR's method (idem, pages 295-299), by condensing a halogenated acylose with a hydroxyl group of phenolic character in the presence of a proton acceptor such as mercuric cyanide, silver imidazolate or silver trifluoro-methylsulfonate;

c) SCHMIDT's method, by condensing an osyl trichloroacetimidate with a hydroxylated aromatic heterocycle in the presence of a Lewis acid such as trimethylsilyl trifluoromethanesulfonate or boron trifluoride etherate.

The compounds of formula I are preferably prepared by methods derived from the processes referred to above.

A first general process comprises carrying out the steps consisting in:

a) reacting a pyridinol of the formula

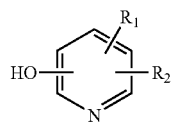

II in which:

$R_1$ is a $C_1$-$C_4$ alkylsulfonyl group, a $C_2$-$C_6$ acyl group, a group CONR'R" or a group

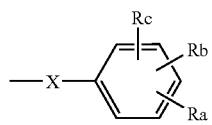

in which:

X is a single bond, an oxygen atom, a sulfoxy group, a group —CO— or a group —CHOH—, Ra is a hydrogen atom, a halogen, a $C_1$-$C_4$ alkyl group, a trifluoromethyl group, a trifluoromethoxy group, a cyano group, a $C_1$-$C_4$ hydroxyalkyl group, a $C_2$-$C_4$ acyl group, a $C_1$-$C_4$ alkoxy group or a group NR'R", Rb and Rc independently of one another are each a hydrogen atom, a halogen atom, a $C_1$-$C_4$ alkyl group, a cyano group or a $C_1$-$C_4$ alkoxy group, $R_2$ is a hydrogen atom, a $C_1$-$C_4$ alkyl group or a halogen atom, and R' and R" independently are each a hydrogen atom or a $C_1$-$C_4$ alkyl group optionally substituted by an aromatic ring, or form, together with the nitrogen atom to which they are attached, a ring having 5 or 6 carbon atoms, with a 5-thioxylopyranose derivative of the formula

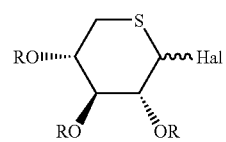

(III-D)

in which Hal is a halogen, preferably bromine, and R is a $C_2$-$C_6$ acyl group, preferably the acetyl group, in an aprotic solvent such as acetonitrile or toluene, in the presence of a silver salt, especially silver oxide or imidazolate, or a zinc salt (especially the oxide or chloride), in an anhydrous medium, at a temperature between 25 and 110° C., for 1 to 10 hours, to give the compound of the formula

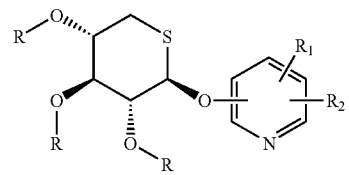

I in which R, $R_1$ and $R_2$ are as defined in the starting compounds;

b) if necessary, reacting the compound of formula I obtained above with a solution of ammonia in methanol to effect deacylation and thus replace the acyl group with hydrogen atoms to give the compound of the formula

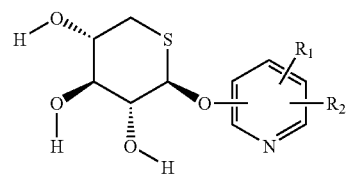

Ia in which $R_1$ and $R_2$ are as defined above; and c) if necessary, reacting one of the compounds I or Ia obtained above with an acid, by methods known to those skilled in the art, to give the corresponding addition salt.

As a variant of step b) described above, the replacement of the acyl group with a hydrogen atom can be effected by reaction with a metal alcoholate, preferably a catalytic amount of sodium methylate in methanol, at a temperature between 0 and 30° C., for 0.5 to 2 hours, to give the compound of formula Ia from the compound of formula I in which R is a $C_2$-$C_6$ acyl group.

In a second process, the compounds of formula I can be obtained by reacting tetra-O-acetyl-5-thioxylopyranose of the formula

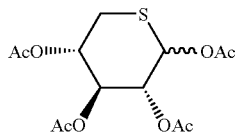

(IV-D)

in which Ac is the acetyl group, with a compound of the formula

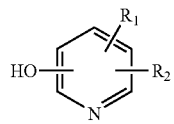

II in which:
R$_1$ is a C$_1$-C$_4$ alkylsulfonyl group, a C$_2$-C$_6$ acyl group, a group CONR'R" or a group

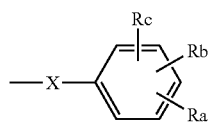

in which:
X is a single bond, an oxygen atom, a sulfoxy group, a group —CO— or a group —CHOH—,
Ra is a hydrogen atom, a halogen, a C$_1$-C$_4$ alkyl group, a trifluoromethyl group, a trifluoromethoxy group, a cyano group, a C$_1$-C$_4$ hydroxyalkyl group, a C$_2$-C$_4$ acyl group, a C$_1$-C$_4$ alkoxy group or a group NR'R",
Rb and Rc independently of one another are each a hydrogen atom, a halogen atom, a C$_1$-C$_4$ alkyl group, a cyano group or a C$_1$-C$_4$ alkoxy group,
R$_2$ is a hydrogen atom, a C$_1$-C$_4$ alkyl group or a halogen atom, and
R' and R" independently are each a hydrogen atom or a C$_1$-C$_4$ alkyl group optionally substituted by an aromatic ring, or form, together with the nitrogen atom to which they are attached, a ring having 5 or 6 carbon atoms,
in an aprotic solvent such as dichloromethane, in the presence of a catalyst of the Lewis acid type, e.g. tin tetrachloride, at a temperature between 20 and 60° C., for 1 to 2 hours, to give the compound of the formula

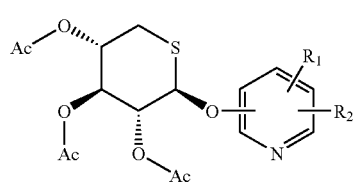

Ib in which R$_1$ and R$_2$ are as defined in the starting compounds.
The compound of formula Ib can then be reacted according to the protocol described in the previous process to give the unsubstituted pyranosyl compound and/or a salt with an acid.
In a third process, the compounds of formula I can be obtained by reacting a thioxylose derivative of the formula

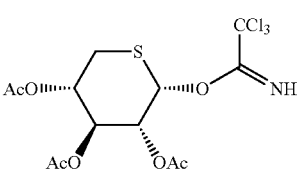

(V-D)

in which Ac is the acetyl group,
with a compound of the formula

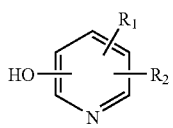

II in which:
R$_1$ is a C$_1$-C$_4$ alkylsulfonyl group, a C$_2$-C$_6$ acyl group, a group CONR'R" or a group

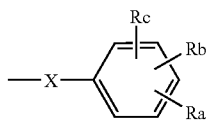

in which:
X is a single bond, an oxygen atom, a sulfoxy group, a group —CO— or a group —CHOH—,
Ra is a hydrogen atom, a halogen, a C$_1$-C$_4$ alkyl group, a trifluoromethyl group, a trifluoromethoxy group, a cyano group, a C$_1$-C$_4$ hydroxyalkyl group, a C$_2$-C$_4$ acyl group, a C$_1$-C$_4$ alkoxy group or a group NR'R",
Rb and Rc independently of one another are each a hydrogen atom, a halogen atom, a C$_1$-C$_4$ alkyl group, a cyano group or a C$_1$-C$_4$ alkoxy group,
R$_2$ is a hydrogen atom, a C$_1$-C$_4$ alkyl group or a halogen atom, and
R' and R" independently are each a hydrogen atom or a C$_1$-C$_4$ alkyl group optionally substituted by an aromatic ring, or form, together with the nitrogen atom to which they are attached, a ring having 5 or 6 carbon atoms, in an aprotic solvent such as dichloromethane, in the presence of a catalyst such as trimethylsilyl trifluoromethanesulfonate, at a temperature between −25° C. and room temperature, for 1 to 5 hours, to give the thioxylopyranoside of the formula

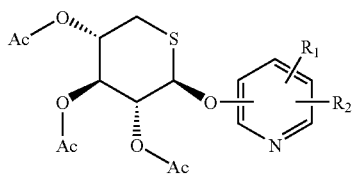

Ib in which R$_1$ and R$_2$ are as defined in the starting compounds.
The resulting compound of formula Ib can then be reacted as above to give the unsubstituted pyranosyl compounds and/or the acid salts.

The compounds of formula I according to the invention in which R₁ is a group

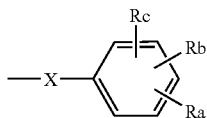

in which X is a single bond can also be prepared from halogenated glycosylated products by means of a Suzuki coupling reaction between two aromatic rings.

One general process comprises carrying out the steps consisting in:

a) reacting a compound of the formula

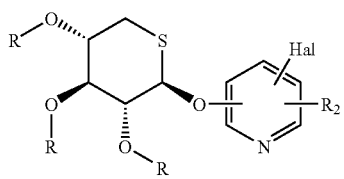

in which Hal is a halogen atom, preferably bromine or iodine, R₂ is a hydrogen atom, a halogen atom (other than bromine or iodine) or a C₁-C₄ alkyl group and R is a hydrogen atom or a C₂-C₆ acyl group,
with a phenylboronic acid derivative or an alkyl phenylboronate of the formula

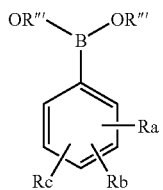

in which:
  Ra is a hydrogen atom, a halogen, a hydroxyl group, a C₁-C₄ alkyl group, a trifluoromethyl group, a trifluoromethoxy group, a cyano group, a C₁-C₄ hydroxy-alkyl group, a C₂-C₄ acyl group, a C₁-C₄ alkoxy group or a group NR'R",
  Rb and Rc independently of one another are each a hydrogen atom, a halogen atom, a C₁-C₄ alkyl group, a cyano group or a C₁-C₄ alkoxy group,
  R' and R" independently are each a hydrogen atom or a C₁-C₄ alkyl group optionally substituted by an aromatic ring, or form, together with the nitrogen atom to which they are attached, a ring having 5 or 6 carbon atoms, and
  R'" is a hydrogen atom or a C₁-C₄ alkyl group,
in the presence of a palladium catalyst such as [1,1-bisdiphenylphosphinoferrocene]dichloropalladium dichloromethane, a palladium catalyst immobilized on resin, or Herrmann's catalyst, in the presence of a polar protic solvent such as methanol, and in the presence of cesium fluoride or sodium carbonate or other mineral bases to which lithium chloride has optionally been added, at a temperature between 70° C. and 150° C., for 5 minutes to 72 hours, with the aid of microwaves or a conventional mode of heating, to give the compound of the formula

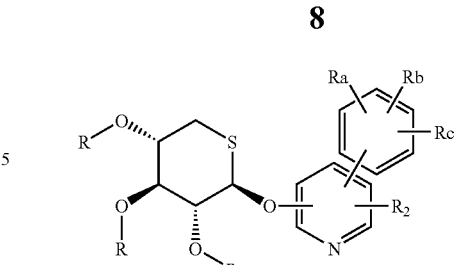

in which:
  Ra, Rb, Rc, R and R₂ are as defined in the starting materials.
  For compounds of this type, another similar process consists in reacting a glycosylated pyridinylboronate of the formula

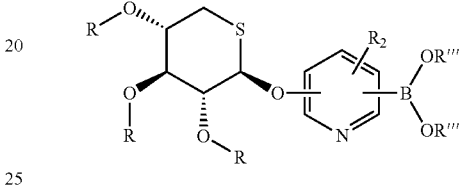

with an aryl halide of the formula

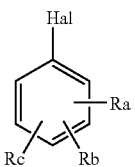

under the same conditions as above, to give the compound of the formula

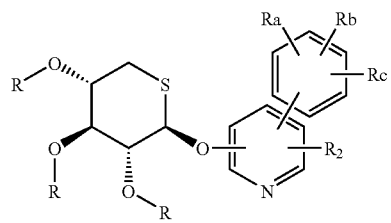

in which:
  Ra, Rb, Rc, R and R₂ are as defined in the starting materials.
  In general terms it is preferable to use 2,3,4-tri-O-acetyl-5-thio-α-D-xylopyranosyl bromide or tetra-O-acetyl-5-thio-α-D-xylopyranose when preparing a β-D-5-thioxylopyranose derivative.

The glycosylation reactions described above most often give rise to a mixture of the isomers of α and β configuration and it is generally necessary to optimize the operating conditions to obtain proportions that favor the isomer of β configuration. For this same reason it may also be necessary to carry out purifications, either by recrystallization or by chromatography, in order to obtain the pure β isomer.

The Examples which follow are intended to illustrate the invention and cannot in any case limit its scope. The melting points were measured on a Koffler bench or in a capillary and the nuclear magnetic resonance spectral values are characterized by the chemical shift calculated relative to TMS, by the number of protons associated with the signal and by the shape of the signal (s for singlet, d for doublet, t for triplet, q for quadruplet, m for multiplet). The operating frequency and the solvent used are indicated for each compound.

The following abbreviations have been used:
mM denotes millimol ($10^{-3}$ mol)
DMSO denotes dimethyl sulfoxide
THF denotes tetrahydrofuran
$CHCl_3$ denotes chloroform
DME denotes dimethoxyethane Preparation 1

(4-bromophenyl)(3-hydroxy-2-pyridinyl)methanone 48.5 g (205.5 mM) of 1,4-dibromobenzene are added dropwise to a mixture containing one crystal of iodine and 5 g (205.5 mM) of magnesium metal covered with 150 ml of THF. The mixture is stirred at the reflux temperature of the solvent for 2 hours and then cooled to 10° C. 12.34 g (102.7 mM) of 2-cyano-3-pyridinol are then added dropwise. The reaction medium is heated at the reflux temperature of the solvent for 3 hours, then stirred for 18 h at room temperature and then treated with 300 ml of 0.5 N sulfuric acid. The solvents are driven off under reduced pressure and the residual aqueous phase is brought to pH 4 by adding a necessary and sufficient amount of 2 N sodium hydroxide solution. The neutralized mixture is extracted with dichloromethane and the organic phase is dried over magnesium sulfate. After evaporation of the solvent, the expected product is obtained in the form of a yellow solid with a yield of 35%.
M.p.=94-95° C.

Preparation 2

4-[(3-hydroxy-2-pyridinyl)carbonyl]benzonitrile 10 g (35.96 mM) of (4-bromophenyl)(3-hydroxy-2-pyridinyl)methanone are mixed with 6.44 g (71.92 mM) of cuprous cyanide in 90 ml of dimethylformamide. The mixture is refluxed for 21 h. A solution of 19.25 g of ferric chloride in 42.5 ml of water and 6.7 ml of concentrated hydrochloric acid is prepared and added to the cooled reaction medium and the resulting mixture is then heated at 90° C. for 30 minutes. After cooling, ethyl acetate and water are added and the mixture is filtered on Celite. The product is then extracted with ethyl acetate and the organic phase is washed with saturated sodium chloride solution. The solvent is evaporated off under reduced pressure to give the desired product in the form of a yellow solid with a yield of 45%.
M.p.=145-146° C.

Preparation 3

(5-hydroxy-2-pyridinyl)[4-(trifluoromethyl)phenyl]methanone

A solution of 23.4 g (104 mM) of 1-bromo-4-trifluoromethylbenzene in 100 ml of THF is added dropwise to 2.53 g (104 mM) of magnesium metal and one crystal of iodine covered with 100 ml of THF. The mixture is stirred at the reflux temperature of the solvent for 2 hours and then cooled to 10° C. A solution of 5 g (42 mM) of 2-cyano-5-pyridinol in 80 ml of THF is then added dropwise. The mixture is refluxed for 2 hours and then stirred for 18 h at room temperature. It is treated with 120 ml of 0.5 N sulfuric acid and the solvents are evaporated off under reduced pressure. The medium is brought to neutral pH by washing with saturated sodium bicarbonate solution, extraction is carried out with ethyl acetate and the extract is dried over magnesium sulfate. After purification by chromatography on silica gel (eluent: toluene/ethyl acetate 8/2, then pure ethyl acetate and finally ethyl acetate/aqueous ammonia 95/5; v/v), the expected product is obtained in the form of a pale pink solid with a yield of 66%.
M.p.>260° C.

Preparation 4

4-(5-methoxy-2-pyridinyl)benzonitrile

A mixture of 3.1 g (13.2 mM) of 2-iodo-5-methoxypyridine, 2.9 g (19.8 mM) of 4-cyanophenylboronic acid, 1.7 g (40 mM) of lithium chloride, 0.6 g (0.52 mM) of tetrakis(triphenylphosphine)palladium, 30 ml of methanol and 30 ml of toluene is prepared and 20 ml (40 mM) of 2 M sodium carbonate are added. The reaction mixture is heated at the reflux temperature of the solvent for 72 hours. The phases are separated and the aqueous phase is extracted with ethyl acetate. The combined organic phases are washed with N sodium hydroxide solution, with water and with saturated sodium chloride solution and then dried over magnesium sulfate. After evaporation of the solvents, the crude product is purified by chromatography on silica gel using dichloromethane as the eluent to give the expected product in the form of a pale yellow solid with a yield of 66%.
M.p.=93-95° C.

Preparation 5

4-(5-hydroxy-2-pyridinyl)benzonitrile

A mixture of 1.82 g (8.65 mM) of the compound obtained according to Preparation 4 and 6 g (52 mM) of pyridinium hydrochloride is heated at 160° C. for 3 h 30 min. It is then cooled to room temperature, taken up with 100 ml of water, adjusted to pH 7 and extracted with ethyl acetate. The organic phase is washed with water and then with saturated sodium chloride solution and dried over magnesium sulfate. After evaporation of the solvents, the product is purified by chromatography on a silica column (eluent: dichloromethane/ethanol 99/1; v/v) to give the expected product in the form of a white powder with a yield of 53%.
M.p.=210° C.

Preparation 6

4-(3-methoxy-2-pyridinyl)benzonitrile

By following a procedure analogous to Preparation 4 starting from 2-bromo-3-methoxypyridine, 4-(3-methoxy-2-pyridinyl)benzonitrile is obtained in the form of a white solid with a yield of 85%.
$^1$H NMR (300 MHz; DMSO) δ=8.34 (dd, 1H); 8.07 (d, 2H); 7.72 (d, 2H); 7.30 (m, 2H); 3.90 (s, 3H).

Preparation 7

4-(3-hydroxy-2-pyridinyl)benzonitrile

By following a procedure analogous to Preparation 5 starting from 4-(3-methoxy-2-pyridinyl)benzonitrile, 4-(3-hydroxy-2-pyridinyl)benzonitrile is obtained in the form of a light beige solid with a yield of 65%.
M.p.=245-246° C.

Preparation 8

4-(5-methoxy-3-pyridinyl)benzonitrile 1.93 g (10.3 mM) of 3-bromo-5-methoxypyridine and 1.85 g (12.36 mM) of 4-cyanophenylboronic acid are mixed with 40 ml of toluene and 40 ml of methanol. 0.6 g (0.5 mM) of tetrakis(triphenylphosphine)palladium and 1.3 g (30.9 mM) of lithium chloride are added. 26 ml of 1 M sodium carbonate solution are then added. The mixture is refluxed for 5 hours and, after cooling, water and ethyl acetate are added to the reaction medium. The aqueous phase is separated off and extracted with ethyl acetate. The combined organic phases are dried over magnesium sulfate and then concentrated under reduced pressure. The evaporation residue is purified by chromatography on silica gel using a dichloromethane/ethyl acetate mixture (94/6; v/v) as the eluent to give the expected product in the form of a beige solid with a yield of 89%.

$^1$H NMR (300 MHz; DMSO) δ=8.56 (m, 1H); 8.36 (m, 1H); 7.98 (m, 4H); 7.73 (m, 1H); 3.92 (s, 3H).

Preparation 9

4-(5-hydroxy-3-pyridinyl)benzonitrile

A mixture of 1.9 g (9.02 mM) of 4-(5-methoxy-3-pyridinyl)benzonitrile and 6.39 g (54.2 mM) of pyridinium hydrochloride is heated at 160° C. for 5 hours. After cooling and the addition of water, the pH is adjusted to 5 with concentrated sodium hydroxide solution. The mixture is extracted with ethyl acetate and the extract is dried over magnesium sulfate and concentrated under reduced pressure. The evaporation residue is purified by chromatography on a silica column (eluent: dichloromethane/ethyl acetate 92/8; v/v, then dichloromethane/methanol 9/1; v/v) to give the expected product in the form of a beige solid with a yield of 76%.

M.p.=241-243° C.

Preparation 10

4-[(5-hydroxy-2-pyridinyl)thio]benzonitrile 0.25 g (1.31 mM) of copper(I) iodide, 7.26 g (52.5 mM) of potassium carbonate and 5.8 g (26.25 mM) of 6-iodo-3-pyridinol are introduced into a tube under an argon atmosphere. 30 ml of isopropanol, 5 g of 1,2-dimethoxyethane and 3.55 g (26.25 mM) of 4-mercaptobenzonitrile are then added. The tube is sealed and heated at 80° C. for 24 hours. When the mixture has returned to room temperature, it is diluted with 120 ml of ethyl acetate and filtered, the solid on the filter is washed with ethyl acetate and the organic phases are concentrated under reduced pressure. The evaporation residue is purified by chromatography on a silica column (eluent: cyclohexanol/ethyl acetate 55/45; v/v) to give the expected product in the form of a beige powder with a yield of 53%.

M.p.=180-181° C.

Preparation 11

4-[(5-hydroxy-2-pyridinyl)sulfonyl]benzonitrile 3.15 g (13.80 mM) of the product obtained according to Preparation 10 are dissolved in 45 ml of acetic acid. 7 ml of hydrogen peroxide are added. The reaction mixture is stirred for six days at room temperature. The precipitate formed is filtered off, washed with water and with petroleum ether and dried to give a first crop of the expected product. The filtrate is brought to pH 5 with dilute sodium hydroxide solution and then extracted with ethyl acetate. The organic phase is dried over magnesium sulfate and concentrated under reduced pressure. The evaporation residue is purified by chromatography on a silica column (eluent: toluene/ethyl acetate 6/4; v/v) to give the expected product in the form of a white powder with an overall yield of 91%.

M.p.=225-226° C.

Preparation 12

2-(methylsulfonyl)-3-pyridinol

A solution of 0.423 g (3 mM) of 2-methylthio-3-pyridinol in 11 ml of ethanol is prepared and a solution of 1.855 g (4.8 mM) of the magnesium salt of monoperoxyphthalic acid in 30 ml of water is added dropwise. The reaction mixture is stirred for 8 hours at room temperature and concentrated under reduced pressure. The residue is purified by chromatography on silica gel using a cyclohexane/acetone mixture (80/20; v/v) as the eluent to give the desired product in the form of a white solid with a yield of 83%.

M.p.=115° C.

Preparation 13

6-(methylthio)-3-pyridinol

A solution of 5.5 ml of concentrated sulfuric acid and 8 ml of water is added to 1.9 g (13.55 mM) of 6-(methylthio)-3-pyridinamine. The reaction medium is brought to −6° C. and a solution of 1.59 g (23.03 mM) of sodium nitrite in 3 ml of water is added dropwise without exceeding 0° C. The mixture is stirred for 1 hour 30 min between 0° C. and −4° C. and then refluxed for 1 hour. The cooled reaction medium is poured in the presence of sodium bicarbonate and the mixture is then extracted with ethyl acetate. The organic phase is concentrated under reduced pressure and the residue is then chromatographed on silica gel (dichloromethane/ethyl acetate, 90/10; v/v) to give the expected product in the form of a white powder with a yield of 60%.

M.p.=133° C.

Preparation 14

6-(methylsulfonyl)-3-pyridinol

By following a procedure analogous to Preparation 12 starting from 6-(methylthio)-3-pyridinol, 6-(methylsulfonyl)-3-pyridinol is obtained in the form of a white powder with a yield of 91%.

M.p.=187° C.

Preparation 15

3-methoxy-5-phenoxypyridine

A solution of 0.9 g (3.6 mM) of 3-bromo-5-phenoxypyridine in 2 ml of methanol is prepared in a microwave tube. 8 ml (8 mM) of a 1 M solution of sodium methylate in methanol and 0.252 g (4 mM) of copper powder are added. The tube is closed and the reaction mixture is heated by microwaves at 150° C. for one hour and then filtered and concentrated under reduced pressure. The concentration residue is taken up with water and extracted with dichloromethane. The organic phase is washed with water, dried over sodium sulfate and concentrated under reduced pressure. The crude product is chromatographed on silica gel using a toluene/ethyl acetate mixture (95/5; v/v) as the eluent to give the expected product in the form of a colorless oil with a quantitative yield.

$^1$H NMR (DMSO, 250 MHz) δ: 8.12 (d, 1H); 7.92 (d, 1H); 7.43 (m, 2H); 7.19 (m, 1H); 7.09 (m, 3H); 3.81 (s, 3H).

Preparation 16

5-phenoxy-3-pyridinol

A mixture of 0.6 g (3.37 mM) of 3-methoxy-5-phenoxypyridine and 1.15 g (10 mM) of pyridinium hydrochloride is prepared. It is heated by microwaves for 40 minutes at 150° C. and then cooled, taken up with methanol and brought to pH 7 with 1 N sodium hydroxide solution. After concentration under reduced pressure, the residue obtained is purified by chromatography on silica gel using a toluene/isopropanol mixture (95/5; v/v) as the eluent to give the desired product in the form of an off-white solid with a yield of 54%.

M.p.=107° C.

Preparation 17

2-chloro-3-fluoro-5-(phenylmethoxy)pyridine 0.5 g (3.38 mM) of 6-chloro-5-fluoro-3-pyridinol, 10 ml of dimethyl-formamide and 0.843 g (6.08 mM) of potassium carbonate are mixed. 0.8 ml (6.76 mM) of benzyl bromide is added and the mixture is heated at 80° C. for one hour. After hydrolysis in 100 ml of water, the mixture is extracted with ethyl acetate and the organic phases are washed with water, dried over magnesium sulfate and concentrated under reduced pressure. The crude product is purified by chromatography on silica gel (eluent: pure toluene) to give the expected product in the form of a white solid with a quantitative yield.

M.p=48-52° C.

Preparation 18

2-phenyl-3-fluoro-5-(phenylmethoxy)pyridine 6.8 g (28.6 mM) of 2-chloro-3-fluoro-5-(phenylmethoxy) pyridine, 110 ml of DME and 4.18 g (34 mM) of phenylboronic acid are mixed. 6.64 g (156 mM) of lithium chloride and 1.65 g (1.4 mM) of tetrakis(triphenylphosphine)palladium are added. Finally, 38 ml (76 mM) of 2 M potassium carbonate solution are added and the mixture is refluxed for 18 hours. After hydrolysis in 250 ml of water, the mixture is extracted with ethyl acetate and the organic phases are washed with water and then with brine, dried over magnesium sulfate, filtered and concentrated under reduced pressure. The residue obtained is purified by chromatography on silica gel using a cyclohexane/ethyl acetate mixture (95/5, then 90/10; v/v) as the eluent to give the desired product in the form of a white solid with a yield of 84%.

M.p.=105-106° C.

Preparation 19

5-fluoro-6-phenyl-3-pyridinol 6.55 g (29.7 mM) of 2-phenyl-3-fluoro-5-(phenylmethoxy)pyridine are added to 160 ml of methanol, 30 ml of ethyl acetate and 30 ml of acetic acid. 0.33 g of 10% palladium-on-charcoal is added. The mixture is stirred under a hydrogen atmosphere for 3 hours. The catalyst is filtered off and the solvents are concentrated to give a white solid, which is taken up with 1 N sodium hydroxide solution. The aqueous phase obtained is washed with dichloromethane and then acidified to pH 5 with 1 N hydrochloric acid solution. The white precipitate obtained is filtered off and washed with water. After drying, the desired product is obtained in the form of a white solid with a yield of 77%.

M.p.=150-151° C.

Preparation 20

5-bromo-2-fluoro-3-pyridinol

A solution of 1.36 g (6.18 mM) of 5-bromo-2-fluoro-3-pyridineboronic acid in a mixture of 9.5 ml of ethanol, 2.3 ml of acetic acid and 1.3 ml of ethyl acetate is prepared. 2.2 ml of 30% hydrogen peroxide are added to the solution. The reaction mixture is stirred at a temperature of 35° C. for 3 hours and then cooled and extracted with ethyl ether. The organic phases are washed with a solution of ferrous ammonium sulfate, dried over magnesium sulfate, filtered and concentrated under reduced pressure. The solid residue is purified by chromatography on silica gel using a toluene/ethyl acetate mixture (9/1; v/v) as the eluent to give the desired product in the form of a white solid with a yield of 62%.

M.p.=146° C.

Preparation 21

4-iodo-3-pyridinyl 2,3,4-tri-O-acetyl-5-thio-β-D-xylopyranoside

By following a procedure analogous to Example 30 starting from 4-iodo-3-pyridinol, 4-iodo-3-pyridinyl 2,3,4-tri-O-acetyl-5-thio-β-D-xylopyranoside is obtained in the form of a white solid (yield=31%).

$[\alpha]_D^{24}$=−63° (c=0.20; DMSO).

M.p.=176° C.

Preparation 22

5-bromo-2-fluoro-3-pyridinyl 2,3,4-tri-O-acetyl-5-thio-β-D-xylopyranoside

By following a procedure analogous to Example 30 starting from 5-bromo-2-fluoro-3-pyridinol, 5-bromo-2-fluoro-3-pyridinyl 2,3,4-tri-O-acetyl-5-thio-β-D-xylopyranoside is obtained in the form of a white solid (yield=39%).

M.p.=120-122° C.

Preparation 23

5-bromo-3-pyridinyl 2,3,4-tri-O-acetyl-5-thio-β-D-xylopyranoside

By following a procedure analogous to Example 30 starting from 5-bromo-3-pyridinol, 5-bromo-3-pyridinyl 2,3,4-tri-O-acetyl-5-thio-β-D-xylopyranoside is obtained in the form of a light brown powder (yield=61%).

M.p.=174° C.

$[\alpha]_D^{20}$=−20° (c=0.20; DMSO).

Preparation 24

2-chloro-4-methyl-3-pyridinyl 2,3,4-tri-O-acetyl-5-thio-β-D-xylopyranoside

By following a procedure analogous to Example 30 starting from 2-chloro-4-methyl-3-pyridinol, 2-chloro-4-methyl-3-pyridinyl 2,3,4-tri-O-acetyl-5-thio-β-D-xylopyranoside is obtained in the form of a white powder (yield=30%).

M.p.=144° C.

$[\alpha]_D^{30}$=+45° (c=0.37; DMSO).

Preparation 25

2-bromo-4-pyridinyl 2,3,4-tri-O-acetyl-5-thio-β-D-xylopyranoside

By following a procedure analogous to Example 30 starting from 2-bromo-4-pyridinol, 2-bromo-4-pyridinyl 2,3,4-tri-O-acetyl-5-thio-β-D-xylopyranoside is obtained in the form of a white solid (yield=37%).

M.p. 162° C.

$[\alpha]_D^{29}$=−11° (c=0.48; DMSO).

Preparation 26

6-bromo-3-pyridinyl 2,3,4-tri-O-acetyl-5-thio-β-D-xylopyranoside

By following a procedure analogous to Example 30 starting from 6-bromo-3-pyridinol, 6-bromo-3-pyridinyl 2,3,4-tri-O-acetyl-5-thio-β-D-xylopyranoside is obtained in the form of a beige powder (yield=43%).

M.p.=145° C.

$[\alpha]_D^{29}$=−20° (c=0.52; DMSO).

Preparation 27

4-bromo-3-pyridinyl 2,3,4-tri-O-acetyl-5-thio-β-D-xylopyranoside

By following a procedure analogous to Example 30 starting from 4-bromo-3-pyridinol, 4-bromo-3-pyridinyl 2,3,4- tri-O-acetyl-5-thio-β-D-xylopyranoside is obtained in the form of a yellow powder (yield=38%).
M.p.=153° C.
$[\alpha]_D^{30}$=−69° (c=0.31; DMSO).
Preparation 28

2-bromo-3-pyridinyl 2,3,4-tri-O-acetyl-5-thio-β-D-xylopyranoside

By following a procedure analogous to Example 30 starting from 2-bromo-3-pyridinol, 2-bromo-3-pyridinyl 2,3,4-tri-O-acetyl-5-thio-β-D-xylopyranoside is obtained in the form of a white powder (yield=41%).
M.p.=156° C.
$[\alpha]_D^{24}$=−78° (c=0.40; CH$_3$OH).
Preparation 29

2-iodo-6-methyl-3-pyridinyl 2,3,4-tri-O-acetyl-5-thio-β-D-xylopyranoside

By following a procedure analogous to Example 30 starting from 2-iodo-6-methyl-3-pyridinol, 2-iodo-6-methyl-3-pyridinyl 2,3,4-tri-O-acetyl-5-thio-β-D-xylopyranoside is obtained in the form of a white powder (yield=81%).
M.p.=187° C.
$[\alpha]_D^{30}$=−88° (c=0.28; DMSO).
Preparation 30

5-methylthio-3-pyridinol 1.284 g (8.2 mM) of 3-methoxy-5-methylthiopyridine and 2.87 g (24.8 mM) of pyridinium hydrochloride are heated at 150° C. for 2 hours in a reactor adapted for microwaves. A saturated aqueous solution of ammonium chloride is added to the cooled reaction medium and the pH is adjusted to neutral with 1 N hydrochloric acid solution. The precipitate formed is filtered off, the filtrate is then extracted with ether and the organic phase is dried over sodium sulfate and then concentrated under reduced pressure. The residue obtained is purified by chromatography on silica gel using a dichloromethane/methanol mixture (99/1, then 80/20; v/v) as the eluent to give the expected product with a yield of 47%.
M.p.=179° C.
Preparation 31

5-methylsulfonyl-3-pyridinol

A solution of 4.018 g (10.39 mM) of the magnesium salt of peroxyphthalic acid in 120 ml of water is added dropwise to a solution of 0.916 g (6.49 mM) of the product obtained according to Preparation 30 in 50 ml of ethanol. The reaction mixture is stirred at 40° C. for 1 hour and then concentrated under reduced pressure. The residue is taken up in a dichloromethane/methanol mixture (10/1; v/v) and filtered. The filtrate is concentrated and then purified by chromatography on silica gel using a toluene/acetone mixture (90/10; v/v) as the eluent to give the expected product in the form of a white solid mixed with phthalic acid, and the product is used without further purification in the synthesis of Example 114.
Preparation 32

5-iodo-3-pyridinyl 2,3,4-tri-O-acetyl-5-thio-β-D-xylopyranoside 1.34 g (3 mM) of 5-bromo-3-pyridinyl 2,3,4-tri-O-acetyl-5-thio-α-D-xylo-pyranoside, 10 ml of dioxane, 0.057 g (0.3 mM) of copper(I) iodide, 0.899 g (6 mM) of sodium iodide and 0.085 g (0.6 mM) of (1R,2R)—N,N'-dimethyl-1,2-cyclohexanediamine are mixed under an argon atmosphere in a reactor adapted for microwaves and the mixture is heated for 3 h 30 min at 130° C. 100 ml of water are added to the cooled reaction mixture and extraction is then carried out with ethyl acetate. The organic phase is washed with 1 N sodium thiosulfate solution and with water, dried over sodium sulfate and then concentrated under reduced pressure. The evaporation residue is purified by chromatography on silica gel using a toluene/acetone mixture (1/1; v/v) as the eluent to give the expected product in the form of a white solid with a yield of 85%.
M.p.=148-150° C.
$[\alpha]_D^{29}$=−7° (c=0.33; DMSO).
Preparation 33

2-iodo-5-triisopropylsilyloxypyridine 5 g (22.6 mM) of 5-hydroxy-2-iodopyridine and 6.42 ml (30.09 mM) of triisopropylsilyl chloride in 35 ml of acetonitrile are stirred at room temperature for 10 minutes. After the addition of 4.62 g (67.87 mM) of imidazole, stirring is maintained for 4 h 20 min at room temperature. The acetonitrile is evaporated off and the reaction mixture is taken up with three 150 ml portions of pentane. The combined organic phases are washed with saturated sodium chloride solution, dried over magnesium sulfate and concentrated under reduced pressure. The evaporation residue is passed through a silica plug using petroleum ether as the eluent to give the desired product in the form of a light yellow oil with a yield of 98%.
$^1$H NMR (250 MHz; DMSO) δ=8.04 (dd, 1H); 7.69 (dd, 1H); 7.08 (dd, 1H); 1.25 (m, 3H); 1.00 (m, 18H).
Preparation 34

5-hydroxy-N-(phenylmethyl)-2-pyridinecarboxamide 3 g (7.95 mM) of the product obtained according to Preparation 33, 3 ml (27.44 mM) of benzylamine, 2.1 g (7.95 mM) of molybdenum hexacarbonyl, 2.25 ml (14.93 mM) of 1,8-diazabicyclo[5,4,0]undec-7-ene (DBU) and 0.373 g (0.4 mM) of trans-di-μ-acetatobis[2-(di-O-tolylphosphino)benzyl]dipalladium(II) (Herrmann's catalyst) are mixed under an argon atmosphere in a reactor adapted for microwaves. The mixture is heated at 150° C. for 15 minutes by microwaves. After cooling, the reaction medium is filtered and concentrated under reduced pressure. The evaporation residue is taken up in methylene chloride and 5 N sodium hydroxide solution. The combined aqueous phases are neutralized in the cold with concentrated hydrochloric acid solution (10 N) and then extracted with ethyl acetate. The organic phase is dried over magnesium sulfate, filtered and concentrated under reduced pressure. The evaporation residue is purified by chromatography on silica gel using pure dichloromethane and then a dichloromethane/methanol mixture (9/1; v/v) as the eluent to give the expected product in the form of an orange solid with a yield of 35%.
$^1$H NMR (250 MHz; DMSO) δ=10.3 (broad, 1H); 9.00 (t, 1H); 8.14 (dd, 1H); 7.90 (dd, 1H); 7.25 (m, 6H); 4.46 (d, 2H).
Preparation 35

5-acetyl-3-pyridinol

A solution of 1.8 g (14.98 mM) of 5-hydroxy-3-pyridinecarbonitrile in 120 ml of THF is added dropwise to a 1.6 M solution of methyllithium in ether (18.7 ml, 29.92 mM), cooled to 0° C. After stirring for 15 minutes, the reaction medium is allowed to warm up to room temperature and stirring is continued for 2 hours. 50 ml of 0.5 N sulfuric acid solution are added to the reaction medium and the pH of the medium is then brought to 6 by adding concentrated hydrochloric acid solution (10 N). The aqueous phase is saturated with sodium chloride and then extracted with ethyl acetate. The organic phase is dried over magnesium sulfate, filtered and concentrated under reduced pressure. The product obtained is then washed with ether and filtered off to give the desired product in the form of a yellow powder with a yield of 75%.

M.p.=186° C.

EXAMPLE 1

6-acetyl-3-pyridinyl 2,3,4-tri-O-acetyl-5-thio-β-D-xylopyranoside 1.29 g (9.47 mM) of zinc chloride are melted and left to cool to room temperature. 4 g of 13× molecular sieve, 50 ml of acetonitrile, 3.1 g (8.7 mM) of 2,3,4-tri-O-acetyl-5-thio-α-D-xylopyranosyl bromide, 1.4 g (8 mM) of silver imidazolate and 1 g (7.3 mM) of 6-acetyl-3-pyridinol are added. The mixture is stirred for 3 hours at 65° C. After filtration, the material on the filter is rinsed with ethyl acetate and the volatile solvents are evaporated off under reduced pressure. The product is purified by chromatography on silica gel using a toluene/isopropanol mixture (98/2; v/v) as the eluent. The purified product is crystallized from isopropyl alcohol to give the expected product in the form of a white solid with a yield of 15%.

M.p.=149° C.
$[\alpha]_D^{22}$=−24° (c=0.1; DMSO).

EXAMPLE 2

6-acetyl-3-pyridinyl 5-thio-β-D-xylopyranoside 0.1 g (0.24 mM) of the product obtained according to Example 1, 5 ml of methanol and a few drops of an 8% solution of sodium methylate in methanol are mixed. The mixture is stirred for 30 minutes at room temperature. The precipitate obtained is filtered off and dried under reduced pressure to give the expected product in the form of white flakes with a yield of 48%.

M.p.=178-179° C.
$[\alpha]_D^{24}$=−76° (c=0.09; DMSO).

EXAMPLE 3

2-acetyl-3-pyridinyl 2,3,4-tri-O-acetyl-5-thio-β-D-xylopyranoside

A mixture of 2.34 g (17.5 mM) of 2-acetyl-3-pyridinol, 8.4 g (19.2 mM) of 5-thio-α-D-xylopyranosyl trichloroacetimidate and 80 ml of dichloromethane is cooled to −20° C. and 316 μl (1.75 mM) of trimethylsilyl trifluoromethanesulfonate are added. The mixture is stirred for 30 minutes at 0° C. and for 4 hours at room temperature. The organic phase is washed with N sodium hydroxide solution and then with water until the pH is neutral. It is dried over magnesium sulfate and the solvent is driven off under reduced pressure. The product is purified by chromatography on a silica column using a cyclohexane/ethyl acetate mixture (6/4; v/v) as the eluent to give the expected product in the form of a yellow solid with a yield of 40%.

M.p.=168° C.
$[\alpha]_D^{23}$=90° (c=0.25; CH$_2$Cl$_2$).

EXAMPLE 4

2-acetyl-3-pyridinyl 5-thio-β-D-xylopyranoside

By following a procedure analogous to Example 2 starting from the product obtained in Example 3, 2-acetyl-3-pyridinyl 5-thio-β-D-xylopyranoside is obtained in the form of a white solid (yield=82%).

M.p.=123° C.
$[\alpha]_D^{23}$=−101° (c=0.44; CH$_3$OH).

EXAMPLE 5

[(4-cyanobenzoyl)-3-pyridinyl]2,3,4-tri-O-acetyl-5-thio-β-D-xylopyranoside

By following a procedure analogous to Example 1 starting from the pyridinol obtained according to Preparation 2, the expected compound is obtained in the form of a white powder (yield=5%).

$[+]_D^{26}$=−35.7° (c=0.11; DMSO).

EXAMPLE 6

[2-(4-cyanobenzoyl)-3-pyridinyl]5-thio-β-D-xylopyranoside 0.23 g (0.46 mM) of the product obtained according to Example 5 is stirred at room temperature for 2 h 30 min with 15 ml of a 7 M solution of ammonia in methanol. The reaction mixture is concentrated under reduced pressure and the crude product obtained is purified by chromatography on silica gel using a dichloromethane/methanol mixture (99/1; v/v) as the eluent. The oil obtained is taken up in solution in 8 ml of hot water and then lyophilized to give the desired product in the form of a yellow powder with a yield of 64%.

M.p.=112° C.
$[\alpha]D^{32}$=−89.5° (c=0.12; DMSO).

EXAMPLE 7

[6-[4-(trifluoromethyl)benzoyl]-3-pyridinyl]2,3,4-tri-O-acetyl-5-thio-β-D-xylopyranoside By following a procedure analogous to Example 1 starting from the compound obtained according to Preparation 3, the expected compound is obtained in the form of white crystals (yield=22%).

$[\alpha]_D^{26}$=−10.1° (c=0.25; DMSO).
M.p.=158-160° C.

EXAMPLE 8

[6-[4-(trifluoromethyl)benzoyl]-3-pyridinyl]5-thio-β-D-xylopyranoside

By following a procedure analogous to Example 2 starting from the product obtained in Example 7, the expected compound is obtained in the form of a white solid (yield=29%).

M.p.=129-132° C.
$[+]_D^{26}$=−293.2° (c=0.12; DMSO).

EXAMPLE 9

[6-(4-cyanophenyl)-3-pyridinyl]2,3,4-tri-O-acetyl-5-thio-β-D-xylopyranoside

By following a procedure analogous to Example 1 starting from the compound obtained according to Preparation 5, the expected product is obtained in the form of a white powder (yield=26%).
$[\alpha]_D^{23}$=+26° (c=0.42; DMSO).
M.p.=197-198° C.

EXAMPLE 10

[6-(4-cyanophenyl)-3-pyridinyl]5-thio-β-D-xylopyranoside

By following a procedure analogous to Example 6 starting from the compound obtained according to Example 9, the expected product is obtained in the form of a white powder (yield=81%).
$[\alpha]_D^{23}$=−32° (c=0.42; DMSO).
M.p.=213-214° C.

EXAMPLE 11

[2-(4-cyanophenyl)-3-pyridinyl]2,3,4-tri-O-acetyl-5-thio-β-D-xylopyranoside

By following a procedure analogous to Example 1 starting from the compound obtained according to Preparation 7, the expected product is obtained in the form of an amorphous solid (yield=10%).
$[\alpha]_D^{26}$=−91.2° (c=0.28; DMSO).
M.p.=120° C.

EXAMPLE 12

[2-(4-cyanophenyl)-3-pyridinyl]5-thio-β-D-xylopyranoside

By following a procedure analogous to Example 6 starting from the compound obtained according to Example 11, the expected product is obtained in the form of a white powder (yield=100%).
$[\alpha]_D^{32}$=−26° (c=0.50; DMSO).
M.p.=180° C.

EXAMPLE 13

5-phenyl-3-pyridinyl 2,3,4-tri-O-acetyl-5-thio-β-D-xylopyranoside

By following a procedure analogous to Example 1 starting from 5-phenyl-3-pyridinol, the expected product is obtained in the form of a white solid (yield=25%).
$[\alpha]_D^{25}$=−9° (c=0.20; DMSO).
M.p.=181° C.

EXAMPLE 14

5-phenyl-3-pyridinyl 5-thio-β-D-xylopyranoside

By following a procedure analogous to Example 2 starting from the compound obtained in Example 13, the expected product is obtained in the form of a white solid (yield=54%).
M.p.=169° C.
$[\alpha]_D^{26}$=−66° (c=0.22; DMSO).

EXAMPLE 15

[5-(4-cyanophenyl)-3-pyridinyl]2,3,4-tri-O-acetyl-5-thio-β-D-xylopyranoside

By following a procedure analogous to Example 1 starting from 5-(4-cyanophenyl)-3-pyridinol, the expected product is obtained in the form of a white powder (yield=27%).
$[\alpha]_D^{23}$=+10° (c=0.39; DMSO).
M.p.=116-117° C.

EXAMPLE 16

[2-(4-cyanophenyl)-3-pyridinyl]5-thio-β-D-xylopyranoside

By following a procedure analogous to Example 6 starting from the compound obtained according to Example 15, the expected product is obtained in the form of a white powder (yield=72%).
$[\alpha]_D^{23}$=−40° (c=0.36; DMSO).
M.p.=202-203° C.

EXAMPLE 17

6-[(4-cyanophenyl)sulfonyl]-3-pyridinyl 2,3,4-tri-O-acetyl-5-thio-β-D-xylo-pyranoside By following a procedure analogous to Example 1 starting from 6-[(4-cyanophenyl)sulfonyl]-3-pyridinol, the expected product is obtained in the form of a white powder (yield=20%).
$[\alpha]_D^{29}$=−19.8° (c=0.24; DMSO).
M.p.=179-180° C.

EXAMPLE 18

6-[(4-cyanophenyl)sulfonyl]-3-pyridinyl 5-thio-β-D-xylopyranoside

By following a procedure analogous to Example 6 starting from the compound obtained in Example 17, the expected product is obtained in the form of a flaky white powder (yield=65%).
$[\alpha]_D^{26}$=−27° (c=0.16; DMSO).
M.p.=179° C.

EXAMPLE 19

2-(methylsulfonyl)-3-pyridinyl 2,3,4-tri-O-acetyl-5-thio-β-D-xylopyranoside

By following a procedure analogous to Example 1 starting from the compound obtained according to Preparation 12, the expected product is obtained in the form of a white powder (yield=53%).
M.p.=172-173° C.

EXAMPLE 20

2-(methylsulfonyl)-3-pyridinyl 5-thio-β-D-xylopyranoside

By following a procedure analogous to Example 2 starting from the compound obtained in Example 19, the expected product is obtained in the form of white flakes (yield=84%).
$[\alpha]_D^{28}$=−70° (c=0.45; $H_2O$).
M.p.=81-105° C.

EXAMPLE 21

6-(methylsulfonyl)-3-pyridinyl 2,3,4-tri-O-acetyl-5-thio-β-D-xylopyranoside

By following a procedure analogous to Example 1 starting from the compound obtained according to Preparation 14, the expected product is obtained in the form of a white powder (yield=51%).
[α]$_D^{21}$=−116° (c=0.46; CHCl$_3$).
M.p.=178° C.

EXAMPLE 22

6-(methylsulfonyl)-3-pyridinyl 5-thio-β-D-xylopyranoside

By following a procedure analogous to Example 2 starting from the 6-(methylsulfonyl)-3-pyridinyl 2,3,4-tri-O-acetyl-5-thio-β-D-xylopyranoside obtained in Example 21, the expected product is obtained in the form of a white powder (yield=98%).
[α]$_D^{24}$=−61°(c=0.43; DMSO).
M.p.=95-114° C.

EXAMPLE 23

2-phenyl-3-pyridinyl 2,3,4-tri-O-acetyl-5-thio-β-D-xylopyranoside 0.1 g (0.24 mM) of 2-chloro-3-pyridinyl 2,3,4-tri-O-acetyl-5-thio-β-D-xylo-pyranoside, 30 ml of DME, 0.037 g (0.29 mM) of phenylboronic acid, 0.102 g (0.66 mM) of cesium fluoride and 0.021 g (0.024 mM) of [1,1'-bis(diphenyl-phosphino)ferrocene]dichloropalladium(II) dichloromethane are mixed. The mixture is heated for 2 hours at 120° C. under an inert atmosphere in a microwave oven. The reaction medium is then filtered on a Whatman filter, the material on the filter is rinsed with ethyl acetate and the filtrate is extracted. The pH is neutralized with ammonium chloride solution. The organic phase is dried over sodium sulfate and the product is concentrated under reduced pressure. It is purified by chromatography on a silica column (eluent: dichloromethane/ethyl acetate 99/1; v/v) to give the expected product in the form of a white powder with a yield of 90%.
M.p.=69-101° C.
[α]$_D^{23}$=−44° (c=0.12; CHCl$_3$).

EXAMPLE 24

2-phenyl-3-pyridinyl 5-thio-β-D-xylopyranoside

By following a procedure analogous to Example 2 starting from the product obtained in Example 23, 2-phenyl-3-pyridinyl 5-thio-β-D-xylopyranoside is obtained in the form of a white solid (yield=89%).
M.p.=89-108° C.
[α]$_D^{25}$=−28° (c=0.2; CH$_3$OH).

EXAMPLE 25

5-phenoxy-3-pyridinyl 2,3,4-tri-O-acetyl 5-thio-β-D-xylopyranoside

By following a procedure analogous to Example 1 starting from 5-phenoxy-3-pyridinol, 5-phenoxy-3-pyridinyl 2,3,4-tri-O-acetyl 5-thio-β-D-xylopyranoside is obtained in the form of a white solid (yield=25%).
[α]$_D^{25}$=−18° (c=0.26; DMSO). M.p.=178° C.

EXAMPLE 26

5-phenoxy-3-pyridinyl 5-thio-β-D-xylopyranoside

By following a procedure analogous to Example 6 starting from the product obtained in Example 25, 5-phenoxy-3-pyridinyl 5-thio-β-D-xylopyranoside is obtained in the form of a white solid (yield=78%).
M.p.=226° C.
[α]$_D^{26}$=−83° (c=0.27; DMSO).

EXAMPLE 27

4-(4-cyanophenyl)-3-pyridinyl 2,3,4-tri-O-acetyl-5-thio-β-D-xylopyranoside

A solution of 0.55 g (1.11 mM) of 4-iodo-3-pyridinyl 2,3,4-tri-O-acetyl-5-thio-β-D-xylopyranoside in 3 ml of DME is prepared and a solution of 0.176 g (1.66 mM) of sodium carbonate in 2.5 ml of water, 0.091 g (0.11 mM) of [1,1'-bis(diphenylphosphino)ferrocene]dichloropalladium(II) dichloromethane and 0.326 g (2.2 mM) of 4-cyanophenylboronic acid are added. The reaction mixture is heated by microwaves at 90° C. for 8 minutes and cooled, water is added and the mixture is extracted with ethyl acetate. The organic phase is washed with 1 M sodium carbonate solution and then with water until the pH is neutral, dried over magnesium sulfate and concentrated under reduced pressure. The product is purified by chromatography on a silica column (eluent: dichloromethane/acetone 80/20; v/v) to give the expected product in the form of an ecru solid with a yield of 63%.
M.p.=212° C.
[α]$_D^{21}$=−113° (c=0.30; DMSO).

EXAMPLE 28

4-(4-cyanophenyl)-3-pyridinyl 5-thio-β-D-xylopyranoside

By following a procedure analogous to Example 6 starting from the product obtained in Example 27, 4-(4-cyanophenyl)-3-pyridinyl 5-thio-β-D-xylopyranoside is obtained in the form of a white solid (yield=90%).
M.p.=238° C.
[α]$_D^{20}$=−97° (c=0.20; DMSO).

EXAMPLE 29

5-[[(phenylmethyl)amino]carbonyl]-3-pyridinyl 5-thio-β-D-xylopyranoside 0.5 g (1.115 mM) of 5-bromo-3-pyridinyl 2,3,4-tri-O-acetyl-5-thio-β-D-xylo-pyranoside, 0.37 ml (3.346 mM) of benzylamine, 0.294 g (1.115 mM) of molybdenum hexacarbonyl, 0.042 g (0.056 mM) of Herrmann's catalyst and 0.5 ml (3.346 mM) of DBU (1,8-diazabicyclo[5.4.0]undec-7-ene) are mixed in 3 ml of THF. The mixture is heated at 150° C. for 15 minutes by microwaves. The reaction mixture is filtered, the filtrate is taken up in 20 ml of ethyl acetate and the organic phase is washed with 1 N sodium hydroxide solution, dried over magnesium sulfate and concentrated under reduced pressure to give the expected product in the form of a pale yellow solid with a yield of 0.7%.
$^1$H NMR (300 MHz; DMSO) δ=9.21 (t, 1H); 8.71 (d, 1H); 8.52 (d, 1H); 7.96 (t, 1H); 7.34 (m, 5H); 5.57 (d, 1H); 5.32 (d, 1H); 5.15 (d, 1H); 5.05 (d, 1H); 4.50 (d, 2H); 3.61 (m, 1H); 3.49 (m, 1H); 3.14 (m, 1H); 2.64 (m, 2H).

EXAMPLE 30

5-fluoro-6-phenyl-3-pyridinyl 2,3,4-tri-O-acetyl-5-thio-β-D-xylopyranoside 2.76 g (19.75 mM) of zinc chloride are melted and cooled under an inert atmosphere and 18 ml of toluene, 18 ml of acetonitrile, 3.16 g of 4 Å molecular sieve and 1.5 g (7.9 mM) of 5-fluoro-6-phenyl-3-pyridinol are then added. This mixture is heated for 5 min at 90° C. and then cooled to room temperature. 2.81 ml (19.75 mM) of triethylamine and 3.16 g (8.69 mM) of 2,3,4-tri-O-acetyl-5-thio-(X-D-xylopyranosyl bromide are then added. The mixture is stirred at 90° C. for 20 minutes and the reaction is then stopped by cooling and by adding 90 ml of 0.5 N sodium hydroxide solution. The reaction medium is filtered to remove the mineral salts, which are washed with ethyl acetate. The combined organic phases are washed with ammonium chloride solution to adjust the pH to 7-8, dried over magnesium sulfate and concentrated under reduced pressure. The product is crystallized from ethyl ether to give the desired product in the form of a beige solid with a yield of 47%.

M.p.=160-162° C.
$[\alpha]_D^{23}$=−58° (c=0.58; $CHCl_3$).

EXAMPLE 31

5-fluoro-6-phenyl-3-pyridinyl 5-thio-β-D-xylopyranoside 1.72 g (3.71 mM) of the product obtained in Example 30 are mixed with 35 ml of methanol. 0.05 ml of a 7 M solution of sodium methylate in methanol is added. The mixture is stirred for 30 minutes at 30° C. The reaction is stopped by adding about 1 g of IR 120 resin. The reaction medium is filtered, the material on the filter is rinsed with methanol and the organic phases are concentrated. The product is recrystallized from ethanol to give the desired product in the form of a white solid with a yield of 61%.

M.p.=174-176° C.
$[\alpha]_D^{23}$=53° (c=0.57; $CH_3OH$).

EXAMPLE 32

5-(4-cyanophenyl)-2-fluoro-3-pyridinyl 2,3,4-tri-O-acetyl-5-thio-β-D-xylo-pyranoside By following a procedure analogous to Example 27 starting from 5-bromo-2-fluoro-3-pyridinyl 2,3,4-tri-O-acetyl-5-thio-β-D-xylopyranoside, 5-(4-cyano-phenyl)-2-fluoro-3-pyridinyl 2,3,4-tri-O-acetyl-5-thio-β-D-xylopyranoside is obtained in the form of a white solid (yield=69%).

M.p.=132-133° C.
$[\alpha]_D^{19}$=−1.3° (c=0.60; $CH_3OH$).

EXAMPLE 33

5-(4-cyanophenyl)-2-fluoro-3-pyridinyl 5-thio-β-D-xylopyranoside

By following a procedure analogous to Example 6 starting from the product obtained in Example 32, 5-(4-cyanophenyl)-2-fluoro-3-pyridinyl 5-thio-β-D-xylo-pyranoside is obtained in the form of a beige solid (yield=73%).

M.p.=220° C.
$[\alpha]_D^{19}$=−62° (c=0.50; $CfH_3OH$).

EXAMPLE 34

4-[4-(trifluoromethyl)phenyl]-3-pyridinyl 2,3,4-tri-O-acetyl-5-thio-β-D-xylo-pyranoside By following a procedure analogous to Example 27 starting from 4-bromo-3-pyridinyl 2,3,4-tri-O-acetyl-5-thio-β-D-xylopyranoside and 4-(trifluoromethyl)-phenylboronic acid, 4-[4-(trifluoromethyl)phenyl]-3-pyridinyl 2,3,4-tri-O-acetyl-5-thio-β-D-xylopyranoside is obtained in the form of a white powder (yield=31%).

M.p. 168° C.
$[\alpha]_D^{22}$−63° (c=0.36; DMSO).

EXAMPLE 35

4-(4-trifluoromethylphenyl)-3-pyridinyl 5-thio-β-D-xylopyranoside

By following a procedure analogous to Example 2 starting from the product obtained in Example 34, 4-(4-trifluoromethylphenyl)-3-pyridinyl 5-thio-β-D-xylo-pyranoside is obtained in the form of a white solid (yield=86%).

M.p.=204° C.
$[\alpha]_D^{22}$2 −70° (c=0.32; DMSO).

EXAMPLE 36

5-(4-trifluoromethoxyphenyl)-3-pyridinyl 5-thio-β-D-xylopyranoside 0.5 g (1.11 mM) of 5-bromo-3-pyridinyl 2,3,4-tri-O-acetyl-5-thio-β-D-xylo-pyranoside, 0.275 g (1.33 mM) of 4-(trifluoromethoxy)phenylboronic acid, 0.373 g (2.45 mM) of cesium fluoride and 0.24 g of tetrakis(triphenylphosphine) palladium catalyst grafted onto polystyrene resin are mixed in 3.5 ml of DME and 5 ml of methanol. The reaction mixture is heated at 110° C. for 20 minutes by microwaves. It is filtered and then concentrated under reduced pressure. The crude product is purified by chromatography on a silica column (eluent: dichloromethane/methanol 90/10; v/v) to give the expected product in the form of a white solid with a yield of 68%.

M.p.=199-202° C.
$[\alpha]_D^{25}$=−67.6° (c=0.10; DMSO).

EXAMPLE 37

5-(3-acetylphenyl)-3-pyridinyl 5-thio-β-D-xylopyranoside

By following a procedure analogous to Example 36 starting from 3-acetyl-phenylboronic acid, 5-(3-acetylphenyl)-3-pyridinyl 5-thio-β-D-xylopyranoside is obtained in the form of a white solid (yield=63%).

M.p.=159-163° C.
$[\alpha]_D^{25}$=−96.7° (c=0.12; DMSO).

EXAMPLE 38

5-(4-fluorophenyl)-3-pyridinyl 5-thio-β-D-xylopyranoside

By following a procedure analogous to Example 36 starting from 4-fluoro-phenylboronic acid, 5-(4-fluorophenyl)-3-pyridinyl 5-thio-β-D-xylopyranoside is obtained in the form of a white solid (yield=41%).

M.p. 208-209° C.
$[\alpha]_D^{25}$=−83.6° (c=0.13; DMSO).

EXAMPLE 39

2-(1-piperidinylcarbonyl)-3-pyridinyl 2,3,4-tri-O-acetyl-5-thio-β-D-xylo-pyranoside By following a procedure analogous to Example 1 starting from 2-(1-piperidinylcarbonyl)-3-pyridinol, the expected compound is obtained in the form of white crystals (yield=35%).
M.p.=89-92° C.
$[\alpha]_D^{25}$=−105.6° (c=0.10; DMSO).

EXAMPLE 40

2-(1-piperidinylcarbonyl)-3-pyridinyl 5-thio-β-D-xylopyranoside

By following a procedure analogous to Example 2 starting from the product obtained in Example 39, the expected compound is obtained in the form of a white solid (yield=38%).
M.p.=81-92° C.
$[\alpha]_D^{19}$=−101.6° (c=0.10; DMSO).

EXAMPLE 41

2-(dimethylaminocarbonyl)-3-pyridinyl 2,3,4-tri-O-acetyl-5-thio-β-D-xylo-pyranoside By following a procedure analogous to Example 1 starting from 2-(dimethylaminocarbonyl)-3-pyridinol, the expected compound is obtained in the form of a white solid (yield=5%).
M.p.=85-89° C.
$[\alpha]_D^{19}$=−69.3° (c=0.10; DMSO).

EXAMPLE 42

2-(dimethylaminocarbonyl)-3-pyridinyl 5-thio-β-D-xylopyranoside

By following a procedure analogous to Example 2 starting from the product obtained in Example 41, 2-(dimethylaminocarbonyl)-3-pyridinyl 5-thio-β-D-xylo-pyranoside is obtained in the form of a white solid (yield=18%).
M.p.=80-85° C.
$[\alpha]_D^{21}$=−31° (c=0.17; DMSO).

EXAMPLE 43

5-(4-methoxyphenyl)-3-pyridinyl 2,3,4-tri-O-acetyl-5-thio-β-D-xylo-pyranoside 1 g (2.23 mM) of 5-bromo-3-pyridinyl 2,3,4-tri-O-acetyl-5-thio-β-D-xylo-pyranoside, 0.4 g (2.67 mM) of 4-methoxyphenylboronic acid, 1.6 g (4.46 mM) of carbonate resin and 0.02 g (0.004 mM) of [1,1-bis(diphenylphosphino)ferrocene]-dichloropalladium(II) dichloromethane are mixed in 7 ml of DME and 5 ml of methanol. The reaction mixture is heated for 20 minutes at 110° C. by microwaves. It is filtered, the material on the filter is rinsed with methanol and the organic phases are concentrated. The product is purified by chromatography on a silica column (eluent: dichloromethane/ethyl acetate 98/2, then 70/30; v/v) to give the expected product in the form of a cream-colored powder with a yield of 80%.
M.p.=156° C.
$[\alpha]_D^{25}$=−11.1° (c=0.42; DMSO).

EXAMPLE 44

5-(4-methoxyphenyl)-3-pyridinyl 5-thio-β-D-xylopyranoside

By following a procedure analogous to Example 2 starting from the product obtained in Example 43, 5-(4-methoxyphenyl)-3-pyridinyl 5-thio-β-D-xylo-pyranoside is obtained in the form of a gray powder (yield=85%).
M.p.=216° C.
$[\alpha]_D^{20}$=−90.9° (c=0.11; DMSO).

EXAMPLE 45

5-(4-hydroxymethylphenyl)-3-pyridinyl 2,3,4-tri-O-acetyl-5-thio-β-D-xylo-pyranoside By following a procedure analogous to Example 43 starting from 4-(hydroxymethyl)phenylboronic acid, 5-(4-hydroxymethylphenyl)-3-pyridinyl 2,3,4-tri-O-acetyl-5-thio-β-D-xylopyranoside is obtained in the form of brown crystals (yield=59%).
M.p.=132-133° C.
$[+]_D^{21}$=−5.3° (c=0.24; DMSO).

EXAMPLE 46

5-(4-hydroxymethylphenyl)-3-pyridinyl 5-thio-β-D-xylopyranoside

By following a procedure analogous to Example 2 starting from the product obtained in Example 45, 5-(4-hydroxymethylphenyl)-3-pyridinyl 5-thio-β-D-xylo-pyranoside is obtained in the form of a pale pink powder (yield=65%).
M.p.=153° C.
$[\alpha]_D^{25}$=−67.5° (c=0.20; DMSO).

EXAMPLE 47

5-[4-(1-piperidinyl)phenyl]-3-pyridinyl 2,3,4-tri-O-acetyl-5-thio-β-D-xylo-pyranoside By following a procedure analogous to Example 43 starting from 4-(1-piperidinyl)phenylboronic acid, the expected compound is obtained in the form of a white solid (yield=15%).
M.p.=196° C.
$[\alpha]_D^{20}$=0° (c=0.17; DMSO).

EXAMPLE 48

5-[4-(1-piperidinyl)phenyl]-3-pyridinyl 5-thio-β-D-xylopyranoside

By following a procedure analogous to Example 6 starting from the compound obtained in Example 47, 5-[4-(1-piperidinyl)phenyl]-3-pyridinyl 5-thio-β-D-xylopyranoside is obtained in the form of a grayish powder (yield=74%).
M.p.=196° C.
$[\alpha]_D^{26}$=−52.5° (c=0.11; DMSO).

EXAMPLE 49

5-[4-(dimethylamino)phenyl]-3-pyridinyl 2,3,4-tri-O-acetyl-5-thio-β-D-xylo-pyranoside By following a procedure analogous to Example 43 starting from 4-(dimethylamino)phenylboronic acid, the expected compound is obtained in the form of a beige powder (yield=25%).
$[\alpha]_D^{22}$=+16° (c 0.33; DMSO).
M.p.=198-199° C.

EXAMPLE 50

5-[4-(dimethylamino)phenyl]-3-pyridinyl 5-thio-β-D-xylopyranoside

By following a procedure analogous to Example 2 starting from the product obtained in Example 49, 5-[4-(dimethylamino)phenyl]-3-pyridinyl 5-thio-β-D-xylopyranoside is obtained in the form of a white powder with a yield of 74%.
M.p.=240° C.
$[\alpha]_D^{23}$=−40° (c=0.40; DMSO).

EXAMPLE 51

5-(4-methylphenyl)-3-pyridinyl 2,3,4-tri-O-acetyl-5-thio-β-D-xylopyranoside

By following a procedure analogous to Example 43 starting from 4-methyl-phenylboronic acid, 5-(4-methylphenyl)-3-pyridinyl 2,3,4-tri-O-acetyl-5-thio-β-D-xylopyranoside is obtained in the form of beige crystals (yield=80%).
M.p.=160-162° C.
$[\alpha]_D^{22}$=−5° (c=0.44; DMSO).

EXAMPLE 52

5-(4-methylphenyl)-3-pyridinyl 5-thio-β-D-xylopyranoside

By following a procedure analogous to Example 2 starting from the product obtained in Example 51, 5-(4-methylphenyl)-3-pyridinyl 5-thio-β-D-xylopyranoside is obtained in the form of a beige powder with a yield of 80%.
M.p.=228° C.
$[\alpha]_D^{22}$=−73° (c=0.41; DMSO).

EXAMPLE 53

5-[4-(trifluoromethyl)phenyl]-3-pyridinyl 2,3,4-tri-O-acetyl-5-thio-β-D-xylo-pyranoside and 5-[4-(trifluoromethyl)phenyl]-3-pyridinyl 5-thio-β-D-xylo-pyranoside By following a procedure analogous to Example 36 starting from 4-(tri-fluoromethyl)phenylboronic acid, 5-[4-(trifluoromethyl)phenyl]-3-pyridinyl 2,3,4-tri-O-acetyl-5-thio-β-D-xylopyranoside is obtained in the form of a white powder (yield=19%, m.p.=163-164° C., $[\alpha]_D^{22}$=−14° (c=+0.44; DMSO)) and 5-[4-(trifluoromethyl)phenyl]-3-pyridinyl 5-thio-β-D-xylopyranoside is obtained in the form of a white powder (yield=17%, m.p.=218-219° C., $[\alpha]_D^{22}$=−62° (c=0.43; DMSO)).

EXAMPLE 54

5-(3-cyanophenyl)-3-pyridinyl 2,3,4-tri-O-acetyl-5-thio-β-D-xylopyranoside

By following a procedure analogous to Example 27 starting from the 5-bromo-3-pyridinyl 2,3,4-tri-O-acetyl-5-thio-β-D-xylopyranoside obtained according to Preparation 23 and 3-cyanophenylboronic acid, 5-(3-cyanophenyl)-3-pyridinyl 2,3,4-tri-O-acetyl-5-thio-β-D-xylopyranoside is obtained in the form of a white solid (yield=59%).
M.p.=130-131° C.
$[\alpha]_D^{30}$=−21° (c=0.10; DMSO).

EXAMPLE 55

5-(3-cyanophenyl)-3-pyridinyl 5-thio-β-D-xylopyranoside

By following a procedure analogous to Example 6 starting from the compound obtained in Example 54, 5-(3-cyanophenyl)-3-pyridinyl 5-thio-β-D-xylopyranoside is obtained in the form of a white solid (yield=67%).
M.p.=172° C.
$[\alpha]_D^{28}$=−87° (c=0.11; DMSO).

EXAMPLE 56

4-(4-fluorophenyl)-3-pyridinyl 2,3,4-tri-O-acetyl-5-thio-β-D-xylopyranoside

By following a procedure analogous to Example 27 starting from the 4-iodo-3-pyridinyl 2,3,4-tri-O-acetyl-5-thio-β-D-xylopyranoside obtained according to Preparation 21 and 4-fluorophenylboronic acid, 4-(4-fluorophenyl)-3-pyridinyl 2,3,4-tri-O-acetyl-5-thio-β-D-xylopyranoside is obtained in the form of a white solid (yield=47%).
M.p.=111° C.
$[\alpha]_D^{30}$=−49° (c=0.30; DMSO).

EXAMPLE 57

4-(4-fluorophenyl)-3-pyridinyl 5-thio-β-D-xylopyranoside

By following a procedure analogous to Example 2 starting from the product obtained in Example 56, 4-(4-fluorophenyl)-3-pyridinyl 5-thio-β-D-xylopyranoside is obtained in the form of a white solid with a yield of 62%.
M.p. 219° C.
$[\alpha]_D^{30}$=−70° (c=0.32; DMSO).

EXAMPLE 58

5-(4-fluoro-3-methylphenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 4-fluoro-3-methyl-phenylboronic acid, 5-(4-fluoro-3-methylphenyl)-3-pyridinyl 2,3,4-tri-O-acetyl-5-thio-β-D-xylopyranoside is obtained in the form of a white solid (yield=48%).
M.p.=161° C.
$[\alpha]_D^{33}$=−16° (c=0.27; DMSO).

EXAMPLE 59

5-(4-fluoro-3-methylphenyl)-3-pyridinyl 5-thio-β-D-xylopyranoside

By following a procedure analogous to Example 6 starting from the compound obtained in Example 58, 5-(4-fluoro-3-methylphenyl)-3-pyridinyl 5-thio-β-D-xylopyranoside is obtained in the form of a white solid (yield=76%).
M.p.=197° C.
$[\alpha]_D^{34}$=−75° (c=0.20; DMSO).

EXAMPLE 60

5-(4-fluoro-2-methylphenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 4-fluoro-2-methyl-phenylboronic acid, 5-(4-fluoro-2-methylphenyl)-3-pyridinyl 2,3,4-tri-O-acetyl-5-thio-β-D-xylopyranoside is obtained in the form of a white solid (yield=72%).
M.p.=120° C.
$[\alpha]_D^{34}$=−20° (c=0.25; DMSO).

EXAMPLE 61

5-(4-fluoro-2-methylphenyl)-3-pyridinyl 5-thio-β-D-xylopyranoside

By following a procedure analogous to Example 6 starting from the compound obtained in Example 60, 5-(4-fluoro-2-methylphenyl)-3-pyridinyl 5-thio-β-D-xylopyranoside is obtained in the form of a white solid (yield=71%).
M.p.=217° C.
$[\alpha]_D^{34}$=−75° (c=0.20; DMSO).

EXAMPLE 62

5-(3-cyano-4-fluorophenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 3-cyano-4-fluoro-phenylboronic acid, 5-(3-cyano-4-fluorophenyl)-3-pyridinyl 2,3,4-tri-O-acetyl-5-thio-β-D-xylopyranoside is obtained in the form of a white powder (yield=66%).
M.p.=178° C.
$[\alpha]_D^{32}$=−13° (c=0.13; DMSO).

EXAMPLE 63

5-(3-cyano-4-fluorophenyl)-3-pyridinyl 5-thio-β-D-xylopyranoside

By following a procedure analogous to Example 6 starting from the compound obtained in Example 62, 5-(3-cyano-4-fluorophenyl)-3-pyridinyl 5-thio-β-D-xylopyranoside is obtained in the form of white crystals (yield=59%).
M.p.=197° C.
$[\alpha]_D^{29}$=−118° (c=0.11; DMSO).

EXAMPLE 64

5-(3-chloro-4-methoxyphenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 3-chloro-4-methoxy-phenylboronic acid, 5-(3-chloro-4-methoxyphenyl)-3-pyridinyl 2,3,4-tri-O-acetyl-5-thio-β-D-xylopyranoside is obtained in the form of a white solid (yield=66%).
M.p.=155° C.
$[\alpha]_D^{32}$=7° (c=0.30; DMSO).

EXAMPLE 65

5-(3-chloro-4-methoxyphenyl)-3-pyridinyl 5-thio-β-D-xylopyranoside

By following a procedure analogous to Example 2 starting from the compound obtained in Example 64, 5-(3-chloro-4-methoxyphenyl)-3-pyridinyl 5-thio-β-D-xylopyranoside is obtained in the form of an ecru solid (yield=60%).
M.p.=165° C.
$[\alpha]_D^{32}$=40° (c=0.34; DMSO).

EXAMPLE 66

5-(3-methoxyphenyl)-3-pyridinyl 2,3,4-tri-O-acetyl-5-thio-β-D-xylo-pyranoside

By following a procedure analogous to Example 27 starting 5-bromo-3-pyridinyl 2,3,4-tri-O-acetyl-5-thio-β-D-xylopyranoside and 3-methoxyphenyl-boronic acid, 5-(3-methoxyphenyl)-3-pyridinyl 2,3,4-tri-O-acetyl-5-thio-β-D-xylopyranoside is obtained in the form of a white powder (yield=77%).
M.p.=112-115° C.
$[\alpha]_D^{32}$=+1° (c=0.12; DMSO).

EXAMPLE 67

5-(3-methoxyphenyl)-3-pyridinyl 5-thio-β-D-xylopyranoside

By following a procedure analogous to Example 2 starting from the compound obtained in Example 66, 5-(3-methoxyphenyl)-3-pyridinyl 5-thio-β-D-xylopyranoside is obtained in the form of a white solid (yield=95%).
M.p.=200° C. (recrystallized from methanol).
$[\alpha]_D^{28}$=−72° (c=0.32; DMSO).

EXAMPLE 68

5-[4-(1-methylethoxy)phenyl]-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 4-methylethoxy-phenylboronic acid, 5-[4-(1-methylethoxy)phenyl]-3-pyridinyl 2,3,4-tri-O-acetyl-5-thio-β-D-xylopyranoside is obtained in the form of a white solid (yield=55%).
M.p. 135° C.
$[\alpha]_D^{28}$=−3° (c=0.35; DMSO).

EXAMPLE 69

5-[4-(1-methylethoxy)phenyl]-3-pyridinyl 5-thio-β-D-xylopyranoside

By following a procedure analogous to Example 2 starting from the compound obtained in Example 68, 5-[4-(1-methylethoxy)phenyl]-3-pyridinyl 5-thio-β-D-xylopyranoside is obtained in the form of a cottony white solid (yield=20%).
M.p.=158° C.
$[\alpha]_D^{29}$=−65° (c=0.42; DMSO).

EXAMPLE 70

5-(3,4-dimethoxyphenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 3,4-dimethoxyphenylboronic acid, 5-(3, 4-dimethoxyphenyl)-3-pyridinyl 2,3,4-tri-O-acetyl-5-thio-β-D-xylopyranoside is obtained in the form of a white solid (yield=73%).
M.p.=145° C.
$[\alpha]_D^{32}$=−8° (c=0.27; DMSO).

EXAMPLE 71

5-(3,4-dimethoxyphenyl)-3-pyridinyl 5-thio-β-D-xylopyranoside

By following a procedure analogous to Example 2 starting from the compound obtained in Example 70, 5-(3,4-dimethoxyphenyl)-3-pyridinyl 5-thio-β-D-xylopyranoside is obtained in the form of a white solid (yield=76%).
M.p.=211° C.
$[\alpha]_D^{29}$=−41° (c=0.35; DMSO).

EXAMPLE 72

2-(4-fluorophenyl)-3-pyridinyl 2,3,4-tri-O-acetyl-5-thio-β-D-xylopyranoside

By following a procedure analogous to Example 27 starting from 2-bromo-3-pyridinyl 2,3,4-tri-O-acetyl-5-thio-β-D-xylopyranoside and 4-fluorophenylboronic acid, 2-(4-fluorophenyl)-3-pyridinyl 2,3,4-tri-O-acetyl-5-thio-β-D-xylopyranoside is obtained in the form of white crystals (yield=64%).
M.p.=149° C.
$[\alpha]_D^{27}$=−91° (c=0.30; DMSO).

EXAMPLE 73

2-(4-fluorophenyl)-3-pyridinyl 5-thio-β-D-xylopyranoside

By following a procedure analogous to Example 6 starting from the compound obtained in Example 72, 2-(4-fluorophenyl)-3-pyridinyl 5-thio-β-D-xylopyranoside is obtained in the form of a white solid (yield=88%).
M.p. 110° C.
$[\alpha]_D^{28}$=−56° (c=0.14; DMSO).

EXAMPLE 74

2-(4-methoxyphenyl)-4-methyl-3-pyridinyl 2,3,4-tri-O-acetyl-5-thio-β-D-xylo-pyranoside By following a procedure analogous to Example 27 starting from the 2-chloro-4-methyl-3-pyridinyl 2,3,4-tri-O-acetyl-5-thio-β-D-xylopyranoside obtained according to Preparation 24 and 4-methoxyphenylboronic acid, 2-(4-methoxy-phenyl)-4-methyl-3-pyridinyl 2,3,4-tri-O-acetyl-5-thio-β-D-xylopyranoside is obtained and is used directly for the deacetylation step.

EXAMPLE 75

2-(4-methoxyphenyl)-4-methyl-3-pyridinyl 5-thio-β-D-xylopyranoside

By following a procedure analogous to Example 6 starting from the compound obtained in Example 74, 2-(4-methoxyphenyl)-4-methyl-3-pyridinyl 5-thio-β-D-xylopyranoside is obtained in the form of a cottony white solid (yield=62%).
M.p.=101° C.
$[\alpha]_D^{31}$=+14° (c=0.14; DMSO).

EXAMPLE 76

2-(4-methoxyphenyl)-4-pyridinyl 2,3,4-tri-O-acetyl-5-thio-β-D-xylopyranoside

By following a procedure analogous to Example 27 starting from the 2-bromo-4-pyridinyl 2,3,4-tri-O-acetyl-5-thio-β-D-xylopyranoside obtained according to Preparation 25 and 4-methoxyphenylboronic acid, 2-(4-methoxyphenyl)-4-pyridinyl 2,3,4-tri-O-acetyl-5-thio-β-D-xylopyranoside is obtained in the form of a beige solid (yield=53%).
M.p.=113-114° C.
$[\beta]_D^{27}$=−9° (c=0.12; DMSO).

EXAMPLE 77

2-(4-methoxyphenyl)-4-pyridinyl 5-thio-β-D-xylopyranoside

By following a procedure analogous to Example 6 starting from the compound obtained in Example 76, 2-(4-methoxyphenyl)-4-pyridinyl 5-thio-β-D-xylopyranoside is obtained in the form of a white solid (yield=33%).
M.p.=150-154° C.
$[\alpha]_D^{27}$=−44° (c=0.11; DMSO).

EXAMPLE 78

5-[3-fluoro-4-(1-methylethoxy)phenyl]-3-pyridinyl 2,3,4-tri-O-acetyl-5-thio-β-D-xylopyranoside By following a procedure analogous to Example 27 starting from 5-bromo-3-pyridinyl 2,3,4-tri-O-acetyl-5-thio-β-D-xylopyranoside and 3-fluoro-4-(1-methyl-ethoxy)phenylboronic acid, 5-[3-fluoro-4-(1-methylethoxy)phenyl]-3-pyridinyl 2,3,4-tri-O-acetyl-5-thio-β-D-xylopyranoside is obtained in the form of a white solid (yield=82%).
M.p.=65° C.
$[\alpha]_D^{29}$=+3° (c=0.22; DMSO).

EXAMPLE 79

5-[3-fluoro-4-(1-methylethoxy)phenyl]-3-pyridinyl 5-thio-β-D-xylopyranoside

By following a procedure analogous to Example 6 starting from the compound obtained in Example 78, 5-[3-fluoro-4-(1-methylethoxyphenyl)]-3-pyridinyl 5-thio-α-D-xylopyranoside is obtained in the form of a white solid (yield=67%).
M.p.=181° C.
$[\alpha]_D^{30}$=−62° (c=0.38; DMSO).

EXAMPLE 80

5-(2,6-difluoro-4-methoxyphenyl)-3-pyridinyl 2,3,4-tri-O-acetyl-5-thio-β-D-xylopyranoside By following a procedure analogous to Example 27 starting from 5-bromo-3-pyridinyl 2,3,4-tri-O-acetyl-5-thio-β-D-xylopyranoside and 2,6-difluoro-4-methoxyphenylboronic acid, 5-(2,6-difluoro-4-methoxyphenyl)-3-pyridinyl 2,3,4-tri-O-acetyl-5-thio-β-D-xylopyranoside is obtained in the form of a white solid (yield=30%).
M.p.=62° C.
$[\alpha]_D^{30}$=−4° (c=0.18; DMSO).

EXAMPLE 81

5-(2,6-difluoro-4-methoxyphenyl)-3-pyridinyl 5-thio-β-D-xylopyranoside

By following a procedure analogous to Example 6 starting from the compound obtained in Example 80, 5-(2,6-difluoro-4-methoxyphenyl)-3-pyridinyl 5-thio-β-D-xylopyranoside is obtained in the form of a white solid (yield=59%).
M.p. 200° C.
$[\alpha]_D^{30} = -59°$ (c=0.36; DMSO).

EXAMPLE 82

5-(3,5-dimethyl-4-methoxyphenyl)-3-pyridinyl 2,3,4-tri-O-acetyl-5-thio-β-D-xylopyranoside By following a procedure analogous to Example 27 starting from 5-bromo-3-pyridinyl 2,3,4-tri-O-acetyl-5-thio-β-D-xylopyranoside and 3,5-dimethyl-4-methoxyphenylboronic acid, 5-(3,5-dimethyl-4-methoxyphenyl)-3-pyridinyl 2,3,4-tri-O-acetyl-5-thio-β-D-xylopyranoside is obtained in the form of a white solid (yield=52%).
M.p.=146° C.
$[\alpha]_D^{29} = 0°$ (c=0.22; DMSO).

EXAMPLE 83

5-(3,5-dimethyl-4-methoxyphenyl)-3-pyridinyl 5-thio-β-D-xylopyranoside

By following a procedure analogous to Example 6 starting from the compound obtained in Example 82, 5-(3,5-dimethyl-4-methoxyphenyl)-3-pyridinyl 5-thio-β-D-xylopyranoside is obtained in the form of a white solid (yield=72%).
M.p.=173° C.
$[\alpha]_D = -63°$ (c=0.23; DMSO).

EXAMPLE 84

5-(2,4-difluorophenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 2,4-difluorophenyl-boronic acid, 5-(2,4-difluorophenyl)-3-pyridinyl 2,3,4-tri-O-acetyl-5-thio-β-D-xylopyranoside is obtained in the form of an off-white foam (yield=87%).
M.p.=121° C.
$[\alpha]_D^{27} = -9°$ (c=0.25; DMSO).

EXAMPLE 85

5-(2,4-difluorophenyl)-3-pyridinyl 5-thio-β-D-xylopyranoside

By following a procedure analogous to Example 2 starting from the compound obtained in Example 84, 5-(2,4-difluorophenyl)-3-pyridinyl 5-thio-β-D-xylopyranoside is obtained in the form of white crystals (yield=79%).
M.p.=221° C.
$[\alpha]_D^{27} = -62°$ (c=0.66; DMSO).

EXAMPLE 86

5-(4-fluoro-2-methoxyphenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 4-fluoro-2-methoxy-phenylboronic acid, 5-(4-fluoro-2-methoxyphenyl)-3-pyridinyl 2,3,4-tri-O-acetyl-5-thio-β-D-xylopyranoside is obtained in the form of an off-white foam (yield=92%).
M.p.=121° C.
$[\alpha]_D^{27} = -11°$ (c=0.23; DMSO).

EXAMPLE 87

5-(4-fluoro-2-methoxyphenyl)-3-pyridinyl 5-thio-β-D-xylopyranoside

By following a procedure analogous to Example 6 starting from the compound obtained in Example 86, 5-(4-fluoro-2-methoxyphenyl)-3-pyridinyl 5-thio-β-D-xylopyranoside is obtained in the form of a white solid (yield=71%).
M.p.=218-228° C. (recrystallized from methanol).
$[\alpha]_D^{27} = +64°$ (c=0.54; DMSO).

EXAMPLE 88

5-(2-chloro-4-fluorophenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 2-chloro-4-fluoro-phenylboronic acid, 5-(2-chloro-4-fluorophenyl)-3-pyridinyl 2,3,4-tri-O-acetyl-5-thio-β-D-xylopyranoside is obtained in the form of an off-white foam (yield 81%).
M.p.=115° C.
$[\alpha]_D^{27} = -11°$ (c=0.38; DMSO).

EXAMPLE 89

5-(2-chloro-4-fluorophenyl)-3-pyridinyl 5-thio-β-D-xylopyranoside

By following a procedure analogous to Example 6 starting from the compound obtained in Example 88, 5-(2-chloro-4-fluorophenyl)-3-pyridinyl 5-thio-β-D-xylopyranoside is obtained in the form of white crystals (yield=78%).
M.p.=208-211° C.
$[\alpha]_D^{27} = -58°$ (c=0.49; DMSO).

EXAMPLE 90

5-(4-cyano-3-fluorophenyl)-3-pyridinyl 2,3,4-tri-O-acetyl-5-thio-β-D-xylo-pyranoside By following a procedure analogous to Example 27 starting from 5-bromo-3-pyridinyl 2,3,4-tri-O-acetyl-5-thio-β-D-xylopyranoside and 3-fluoro-4-cyano-phenylboronic acid, 5-(4-cyano-3-fluorophenyl)-3-pyridinyl 2,3,4-tri-O-acetyl-5-thio-β-D-xylopyranoside is obtained in the form of a cream-colored solid (yield=65%).
M.p.=223° C.
$[\alpha]_D^{26} = -20°$ (c=0.23; DMSO).

EXAMPLE 91

5-(4-cyano-3-fluorophenyl)-3-pyridinyl 5-thio-β-D-xylopyranoside

By following a procedure analogous to Example 2 starting from the compound obtained in Example 90, 5-(4-cyano-3- fluorophenyl)-3-pyridinyl 5-thio-β-D-xylopyranoside is obtained in the form of white crystals (yield=75%).
M.p.=214° C.
$[\alpha]_D^{21}=-51°$ (c=0.16; DMSO).

EXAMPLE 92

6-(4-methoxyphenyl)-3-pyridinyl 2,3,4-tri-O-acetyl-5-thio-β-D-xylo-pyranoside

By following a procedure analogous to Example 43 starting from 4-methoxyphenylboronic acid and the 6-bromo-3-pyridinyl 2,3,4-tri-O-acetyl-5-thio-β-D-xylopyranoside obtained according to Preparation 26, 6-(4-methoxyphenyl)-3-pyridinyl 2,3,4-tri-O-acetyl-5-thio-β-D-xylopyranoside is obtained in the form of a whitish powder (yield=28%).
M.p.=208° C. (crystallized from ethyl acetate).
$[\alpha]_D^{29}=+12°$ (c=0.25; DMSO).

EXAMPLE 93

6-(4-methoxyphenyl)-3-pyridinyl 5-thio-β-D-xylopyranoside

By following a procedure analogous to Example 2 starting from the compound obtained in Example 92, 6-(4-methoxyphenyl)-3-pyridinyl 5-thio-β-D-xylopyranoside is obtained in the form of a white powder (yield=74%).
M.p.=164° C.
$[\alpha]_D^{29}=-37°$ (c=0.23; DMSO).

EXAMPLE 94

6-[4-(hydroxymethyl)phenyl]-3-pyridinyl 2,3,4-tri-O-acetyl-5-thio-β-D-xylo-pyranoside By following a procedure analogous to Example 43 starting from 4-(hydroxymethyl)phenylboronic acid and the 6-bromo-3-pyridinyl 2,3,4-tri-O-acetyl-5-thio-β-D-xylopyranoside obtained according to Preparation 26, 6-[4-(hydroxymethyl)phenyl]-3-pyridinyl 2,3,4-tri-O-acetyl-5-thio-β-D-xylopyranoside is obtained in the form of a white powder (yield=29%).
M.p.=157° C.
$[\alpha]_D^{29}=+12°$ (c=0.42; DMSO).

EXAMPLE 95

6-[4-(hydroxymethyl)phenyl]-3-pyridinyl 5-thio-β-D-xylopyranoside

By following a procedure analogous to Example 2 starting from the compound obtained in Example 94, 6-[4-(hydroxymethyl)phenyl]-3-pyridinyl 5-thio-β-D-xylopyranoside is obtained in the form of a white powder (yield=68%).
M.p.=215° C. (crystallized from water).
$[\alpha]_D^{28}=-18°$ (c=0.17; DMSO).

EXAMPLE 96

6-[4-(trifluoromethyl)phenyl]-3-pyridinyl 2,3,4-tri-O-acetyl-5-thio-β-D-xylo-pyranoside By following a procedure analogous to Example 43 starting from 4-(trifluoromethyl)phenylboronic acid and the 6-bromo-3-pyridinyl 2,3,4-tri-O-acetyl-5-thio-β-D-xylopyranoside obtained according to Preparation 26, 6-[4-(trifluoromethyl)phenyl]-3-pyridinyl 2,3,4-tri-O-acetyl-5-thio-β-D-xylopyranoside is obtained in the form of a white powder (yield=25%).
M.p.=178-180° C.
$[\alpha]_D^{23}=+7°$ (c=0.34; DMSO).

EXAMPLE 97

6-[4-(trifluoromethyl)phenyl]-3-pyridinyl 5-thio-α-D-xylopyranoside

By following a procedure analogous to Example 2 starting from the compound obtained in Example 96, 6-[4-(trifluoromethyl)phenyl]-3-pyridinyl 5-thio-β-D-xylopyranoside is obtained in the form of a white powder (yield=90%).
M.p.=194-195° C. (crystallized from methanol).
$[\alpha]_D^{28}=-41°$ (c=0.34; DMSO).

EXAMPLE 98

6-(4-methylphenyl)-3-pyridinyl 2,3,4-tri-O-acetyl-5-thio-α-D-xylopyranoside

By following a procedure analogous to Example 43 starting from 4-methyl-phenylboronic acid and the 6-bromo-3-pyridinyl 2,3,4-tri-O-acetyl-5-thio-β-D-xylopyranoside obtained according to Preparation 26, 6-(4-methylphenyl)-3-pyridinyl 2,3,4-tri-O-acetyl-5-thio-β-D-xylopyranoside is obtained in the form of a white powder (yield=25%).
M.p.=150-152° C.
$[\alpha]_D^{31}=+10°$ (c=0.32; DMSO).

EXAMPLE 99

6-(4-methylphenyl)-3-pyridinyl 5-thio-β-D-xylopyranoside

By following a procedure analogous to Example 2 starting from the compound obtained in Example 98, 6-(4-methylphenyl)-3-pyridinyl 5-thio-β-D-xylopyranoside is obtained in the form of a white powder (yield=84%).
M.p.=191° C.
$[\alpha]_D^{30}=48°$ (c=0.33; DMSO).

EXAMPLE 100

4-(4-methoxyphenyl)-3-pyridinyl 2,3,4-tri-O-acetyl-5-thio-β-D-xylo-pyranoside

By following a procedure analogous to Example 43 starting from 4-methoxyphenylboronic acid and the 4-bromo-3-pyridinyl 2,3,4-tri-O-acetyl-5-thio-β-D-xylopyranoside obtained according to Preparation 27, 4-(4-methoxyphenyl)-3-pyridinyl 2,3,4-tri-O-acetyl-5-thio-β-D-xylopyranoside is obtained in the form of a white solid (yield=29%).
M.p. 193° C. (crystallized from 2-propanol).
$[\alpha]_D^{30}=93°$ (c=0.26; DMSO).

EXAMPLE 101

4-(4-methoxyphenyl)-3-pyridinyl 5-thio-β-D-xylopyranoside

By following a procedure analogous to Example 2 starting from the compound obtained in Example 100, 4-(4-methoxyphenyl)-3-pyridinyl 5-thio-β-D-xylopyranoside is obtained in the form of a pink powder (yield=66%).
M.p.=228° C. (crystallized from methanol).
$[\alpha]_D^{32}$=−80° (c=0.54; DMSO).

EXAMPLE 102

5-(3-fluoro-4-methoxyphenyl)-3-pyridinyl 2,3,4-tri-O-acetyl-5-thio-β-D-xylo-pyranoside By following a procedure analogous to Example 43 starting from 3-fluoro-4-methoxyphenylboronic acid, 5-(3-fluoro-4-methoxyphenyl)-3-pyridinyl 2,3,4-tri-O-acetyl-5-thio-β-D-xylopyranoside is obtained in the form of a pale pink powder (yield=64%).
M.p.=150-152° C.
$[\alpha]_D^{31}$=+5° (c=0.16; DMSO).

EXAMPLE 103

5-(3-fluoro-4-methoxyphenyl)-3-pyridinyl 5-thio-β-D-xylopyranoside

By following a procedure analogous to Example 6 starting from the compound obtained in Example 102, 5-(3-fluoro-4-methoxyphenyl)-3-pyridinyl 5-thio-β-D-xylopyranoside is obtained in the form of a white solid (yield=80%).
M.p.=200° C. (crystallized from methanol).
$[\alpha]_D^{28}$=−3° (c=0.48; DMSO).

EXAMPLE 104

5-(4-methoxy-2-methylphenyl)-3-pyridinyl 2,3,4-tri-O-acetyl-5-thio-β-D-xylo-pyranoside By following a procedure analogous to Example 43 starting from 4-methoxy-2-methylphenylboronic acid, 5-(4-methoxy-2-methylphenyl)-3-pyridinyl 2,3,4-tri-O-acetyl-5-thio-β-D-xylopyranoside is obtained in the form of a white powder (yield=32%).
M.p.=283° C. (crystallized from 2-propanol).
$[\alpha]_D^{29}$=−6° (c=0.35; DMSO).

EXAMPLE 105

5-(4-methoxy-2-methylphenyl)-3-pyridinyl 5-thio-β-D-xylopyranoside

By following a procedure analogous to Example 2 starting from the compound obtained in Example 104, 5-(4-methoxy-2-methylphenyl)-3-pyridinyl 5-thio-β-D-xylopyranoside is obtained in the form of a gray powder (yield=68%).
M.p.=231° C. (crystallized from water).
$[\alpha]_D^{29}$=−57° (c=0.32; DMSO).

EXAMPLE 106

5-(3-fluoro-4-methylphenyl)-3-pyridinyl 2,3,4-tri-O-acetyl-5-thio-β-D-xylo-pyranoside By following a procedure analogous to Example 43 starting from 3-fluoro-4-methylphenylboronic acid, 5-(3-fluoro-4-methylphenyl)-3-pyridinyl 2,3,4-tri-O-acetyl-5-thio-β-D-xylopyranoside is obtained in the form of a pink powder (yield=31%).
M.p.=159° C.
$[\alpha]_D^{27}$=−14° (c=0.19; DMSO).

EXAMPLE 107

5-(3-fluoro-4-methylphenyl)-3-pyridinyl 5-thio-β-D-xylopyranoside

By following a procedure analogous to Example 2 starting from the compound obtained in Example 106, 5-(3-fluoro-4-methylphenyl)-3-pyridinyl 5-thio-β-D-xylopyranoside is obtained in the form of gray crystals (yield=25%).
M.p.=213° C. (crystallized from 2-propanol).
$[\alpha]_D^{30}$=−22° (c=0.17; DMSO).

EXAMPLE 108

5-(3,4-dimethylphenyl)-3-pyridinyl 2,3,4-tri-O-acetyl-5-thio-β-D-xylo-pyranoside By following a procedure analogous to Example 43 starting from 3,4-dimethylphenylboronic acid, 5-(3,4-dimethylphenyl)-3-pyridinyl 2,3,4-tri-O-acetyl-5-thio-β-D-xylopyranoside is obtained in the form of a white solid (yield=50%).
M.p.=131° C.
$[\alpha]_D^{27}$=−5° (c=0.15; DMSO).

EXAMPLE 109

5-(3,4-dimethylphenyl)-3-pyridinyl 5-thio-β-D-xylopyranoside

By following a procedure analogous to Example 2 starting from the compound obtained in Example 108, 5-(3,4-dimethylphenyl)-3-pyridinyl 5-thio-β-D-xylopyranoside is obtained in the form of a white solid (yield=31%).
M.p. 184° C.
$[\alpha]_D^{28}$=−57° (c=0.22; DMSO).

EXAMPLE 110

5-(2-chloro-4-methylphenyl)-3-pyridinyl 2,3,4-tri-O-acetyl-5-thio-β-D-xylo-pyranoside By following a procedure analogous to Example 43 starting from 2-chloro-4-methylphenylboronic acid, 5-(2-chloro-4-methylphenyl)-3-pyridinyl 2,3,4-tri-O-acetyl-5-thio-β-D-xylopyranoside is obtained in the form of a beige powder (yield=50%).
M.p.=162° C.
$[\alpha]_D^{30}$=−8° (c=0.27; DMSO).

EXAMPLE 111

5-(2-chloro-4-methylphenyl)-3-pyridinyl 5-thio-β-D-xylopyranoside

By following a procedure analogous to Example 6 starting from the compound obtained in Example 110, 5-(2-chloro-4-methylphenyl)-3-pyridinyl 5-thio-β-D-xylopyranoside is obtained in the form of a white powder (yield=58%).
M.p.=207° C.
$[\alpha]_D^{30}$=−48° (c=0.15; DMSO).

EXAMPLE 112

5-(2-chloro-4-methoxyphenyl)-3-pyridinyl 2,3,4-tri-O-acetyl-5-thio-β-D-xylo-pyranoside By following a procedure analogous to Example 43 starting from 2-chloro-4-methoxyphenylboronic acid, 5-(2-chloro-4-methoxyphenyl)-3-pyridinyl 2,3,4-tri-O-acetyl-5- thio-β-D-xylopyranoside is obtained in the form of a white powder (yield=32%).

M.p.=126° C.

$[\alpha]_D^{30}=-11°$ (c=0.41; DMSO).

EXAMPLE 113

5-(2-chloro-4-methoxyphenyl)-3-pyridinyl 5-thio-β-D-xylopyranoside

By following a procedure analogous to Example 2 starting from the compound obtained in Example 112, 5-(2-chloro-4-methoxyphenyl)-3-pyridinyl 5-thio-β-D-xylopyranoside is obtained in the form of beige needles (yield=53%).

M.p.=218° C. (crystallized from an ethanol/water mixture).

$[\alpha]_D^{26}=-43°$ (c=0.16; DMSO).

EXAMPLE 114

5-methylsulfonyl-3-pyridinyl 2,3,4-tri-O-acetyl-5-thio-β-D-xylopyranoside

By following a procedure analogous to Example 30 starting from the 5-methylsulfonyl-3-pyridinol obtained according to Preparation 31,5-methylsulfonyl-3-pyridinyl 2,3,4-tri-O-acetyl-5-thio-β-D-xylopyranoside is obtained in the form of a cream-colored powder (yield=18%).

M.p.=193° C.

$[\alpha]_D^{29}=+162°$ (c=0.50; CHCl$_3$).

EXAMPLE 115

5-methylsulfonyl-3-pyridinyl 5-thio-β-D-xylopyranoside

By following a procedure analogous to Example 2 starting from the compound obtained in Example 114, 5-methylsulfonyl-3-pyridinyl 5-thio-β-D-xylopyranoside is obtained in the form of white flakes (yield=90%).

M.p.=183° C.

$[\alpha]_D^{29}=+248°$ (c=0.30; H$_2$O).

EXAMPLE 116

6-{[(phenylmethyl)amino]carbonyl}-3-pyridinyl 2,3,4-tri-O-acetyl-5-thio-β-D-xylopyranoside By following a procedure analogous to Example 30 starting from 2,3,4-tri-O-acetyl-5-thio-β-D-xylopyranosyl bromide and the 5-hydroxy-N-(phenylmethyl)-2-pyridinecarboxamide obtained according to Preparation 34, 6-{[(phenylmethyl)amino]carbonyl}-3-pyridinyl 2,3,4-tri-O-acetyl-5-thio-β-D-xylopyranoside is obtained in the form of a beige solid (yield=31%).

M.p.=177-178° C.

$[\alpha]_D^{30}=-13°$ (c=0.17; DMSO).

EXAMPLE 117

6-{[(phenylmethyl)amino]carbonyl}-3-pyridinyl 5-thio-β-D-xylopyranoside

By following a procedure analogous to Example 2 starting from the compound obtained in Example 116, 6-{[(phenylmethyl)amino]carbonyl}-3-pyridinyl 5-thio-β-D-xylopyranoside is obtained in the form of yellow crystals (yield=86%).

M.p. 89-91° C.

$[\alpha]_D^{30}=-52°$ (c=0.15; DMSO).

EXAMPLE 118

5-acetyl-3-pyridinyl 2,3,4-tri-O-acetyl-5-thio-β-D-xylopyranoside

By following a procedure analogous to Example 30 starting from the 5-acetyl-3-pyridinol obtained according to Preparation 35,5-acetyl-3-pyridinyl 2,3,4-tri-O-acetyl-5-thio-β-D-xylopyranoside is obtained in the form of a light yellow powder (yield=20%).

M.p.=157° C.

$[\alpha]_D^{27}=-7°$ (c=0.21; DMSO).

EXAMPLE 119

5-acetyl-3-pyridinyl 5-thio-β-D-xylopyranoside

By following a procedure analogous to Example 2 starting from the compound obtained in Example 118, 5-acetyl-3-pyridinyl 5-thio-β-D-xylo-pyranoside is obtained in the form of pink needles (yield=50%).

M.p.=209° C.

$[\alpha]_D^{27}=-93°$ (c=0.19; DMSO).

EXAMPLE 120

4-acetyl-3-pyridinyl 2,3,4-tri-O-acetyl-5-thio-β-D-xylopyranoside

By following a procedure analogous to Example 30 starting from 4-acetyl-3-pyridinol, 4-acetyl-3-pyridinyl 2,3,4-tri-O-acetyl-5-thio-β-D-xylopyranoside is obtained and is used directly in the deacetylation step without intermediate purification.

EXAMPLE 121

4-acetyl-3-pyridinyl 5-thio-β-D-xylopyranoside

By following a procedure analogous to Example 6 starting from the compound obtained in Example 120, 4-acetyl-3-pyridinyl 5-thio-β-D-xylo-pyranoside is obtained in the form of a yellow powder (yield=23%).

M.p.=163° C. (crystallized from 2-propanol).

$[\alpha]_D^{29}=-83°$ (c=0.23; DMSO).

EXAMPLE 122

2-(4-methoxyphenyl)-3-pyridinyl 5-thio-β-D-xylopyranoside

A mixture of 0.8 g (1.8 mM) of the 2-bromo-3-pyridinyl 2,3,4-tri-O-acetyl-5-thio-β-D-xylopyranoside obtained according to Preparation 28, 0.325 g (2.14 mM) of 4-methoxyphenylboronic acid, 0.8 g (0.08 mM) of Suzuki's catalyst supported on resin (Argonaut, PSPPh$_3$Pd resin), 1.16 g (3.56 mM) of cesium carbonate, 5 ml of DME and 4 ml of methanol is placed in a reactor adapted for microwaves. The mixture is heated at 120° C. for 30 minutes by microwaves. After filtration, rinsing with methanol and evaporation of the solvents, the residue obtained is chromatographed directly on silica gel using firstly pure dichloro-methane and then a dichloromethane/methanol mixture (9/1; v/v) as the eluent. The foam obtained is crystallized from ether to give the expected product in the form of a white powder (yield=65%).
M.p.=137° C.
$[\alpha]_D^{33}=-79°$ (c=0.17; DMSO).

EXAMPLE 123

5-(3-fluorophenyl)-3-pyridinyl 5-thio-β-D-xylopyranoside

By following a procedure analogous to Example 122 starting from 3-fluoro-phenylboronic acid and 5-bromo-3-pyridinyl 2,3,4-tri-O-acetyl-5-thio-β-D-xylo-pyranoside, 5-(3-fluorophenyl)-3-pyridinyl 5-thio-β-D-xylopyranoside is obtained in the form of a white solid (yield=67%).
M.p.=182-184° C.
$[\alpha]_D^{28}=-55°$ (c=0.11; DMSO).

EXAMPLE 124

6-(3-acetylphenyl)-3-pyridinyl 5-thio-β-D-xylopyranoside

By following a procedure analogous to Example 122 starting from 3-acetyl-phenylboronic acid and the 6-bromo-3-pyridinyl 2,3,4-tri-O-acetyl-5-thio-β-D-xylopyranoside obtained according to Preparation 26, 6-(3-acetylphenyl)-3-pyridinyl 5-thio-β-D-xylopyranoside is obtained in the form of a white solid (yield=44%).
M.p.=159-163° C. (crystallized from water).
$[\alpha]_D^{31}=-38°$ (c=0.10; DMSO).

EXAMPLE 125

6-[4-(trifluoromethoxy)phenyl]-3-pyridinyl 5-thio-β-D-xylopyranoside

By following a procedure analogous to Example 122 starting from 4-(trifluoromethoxy)phenylboronic acid and the 6-bromo-3-pyridinyl 2,3,4-tri-O-acetyl-5-thio-β-D-xylopyranoside obtained according to Preparation 26, 6-[4-(trifluoromethoxy)phenyl]-3-pyridinyl 5-thio-β-D-xylopyranoside is obtained in the form of white crystals (yield=31%).
M.p.=184-186° C. (crystallized from water).
$[\alpha]_{31}=-34°$ (c=0.10; DMSO).

EXAMPLE 126

5-(2-fluorophenyl)-3-pyridinyl 5-thio-β-D-xylopyranoside

By following a procedure analogous to Example 122 starting from 2-fluoro-phenylboronic acid and 5-bromo-3-pyridinyl 2,3,4-tri-O-acetyl-5-thio-β-D-xylo-pyranoside, 5-(2-fluorophenyl)-3-pyridinyl 5-thio-β-D-xylopyranoside is obtained in the form of a white powder (yield=51%).
M.p.=206-208° C.
$[\alpha]_D^{32}=-63°$ (c=0.17; DMSO).

EXAMPLE 127

2-[4-(trifluoromethoxy)phenyl]-3-pyridinyl 5-thio-β-D-xylopyranoside

By following a procedure analogous to Example 122 starting from 4-(trifluoromethoxy)phenylboronic acid and the 2-bromo-3-pyridinyl 2,3,4-tri-O-acetyl-5-thio-β-D-xylopyranoside obtained according to Preparation 28, 2-[4-(trifluoromethoxy)phenyl]-3-pyridinyl 5-thio-β-D-xylopyranoside is obtained in the form of white crystals (yield=33%).
M.p.=114-119° C. (crystallized from water).
$[\alpha]_D^{30}=-38°$ (c=0.15; DMSO).

EXAMPLE 128

2-(3-acetylphenyl)-3-pyridinyl 5-thio-β-D-xylopyranoside

By following a procedure analogous to Example 122 starting from 3-acetyl-phenylboronic acid and the 2-bromo-3-pyridinyl 2,3,4-tri-O-acetyl-5-thio-β-D-xylopyranoside obtained according to Preparation 28, 2-(3-acetylphenyl)-3-pyridinyl 5-thio-β-D-xylopyranoside is obtained in the form of white crystals (yield=44%).
M.p. 128-133° C. (crystallized from water).
$[\alpha]_D^{30}$ 117° (c=0.10; DMSO).

EXAMPLE 129

6-(4-fluorophenyl)-3-pyridinyl 5-thio-β-D-xylopyranoside

By following a procedure analogous to Example 122 starting from 4-fluoro-phenylboronic acid and the 6-bromo-3-pyridinyl 2,3,4-tri-O-acetyl-5-thio-β-D-xylopyranoside obtained according to Preparation 26, 6-(4-fluorophenyl)-3-pyridinyl 5-thio-β-D-xylopyranoside is obtained in the form of a white solid (yield=46%).
M.p.=180-183° C.
$[\alpha]_D^{28}=-50°$ (c=0.10; DMSO).

EXAMPLE 130

5-(2-cyanophenyl)-3-pyridinyl 5-thio-β-D-xylopyranoside

By following a procedure analogous to Example 122 starting from 2-cyano-phenylboronic acid and 5-bromo-3-pyridinyl 2,3,4-tri-O-acetyl-5-thio-β-D-xylo-pyranoside, 5-(2-cyanophenyl)-3-pyridinyl 5-thio-β-D-xylopyranoside is obtained in the form of a white solid (yield=67%).
M.p.=177-179° C.
$[\alpha]_D^{28}=-74°$ (c=0.15; DMSO).

EXAMPLE 131

5-(3-chloro-4-fluorophenyl)-3-pyridinyl 5-thio-β-D-xylopyranoside

By following a procedure analogous to Example 122 starting from 3-chloro-4-fluorophenylboronic acid and 5-bromo-3-pyridinyl 2,3,4-tri-O-acetyl-5-thio-β-D-xylopyranoside, 5-(3-chloro-4-fluorophenyl)-3-pyridinyl 5-thio-β-D-xylopyranoside is obtained in the form of a white powder (yield=59%).
M.p.=200-201° C.
$[\alpha]_D^{28}=74°$ (c=0.18; DMSO).

EXAMPLE 132

5-(3,4-difluorophenyl)-3-pyridinyl 5-thio-β-D-xylopyranoside

By following a procedure analogous to Example 122 starting from 3,4-difluorophenylboronic acid and 5-bromo-3-pyridinyl 2,3,4-tri-O-acetyl-5-thio-β-D-xylopyranoside, 5-(3,4-difluorophenyl)-3-pyridinyl 5-thio-β-D-xylopyranoside is obtained in the form of a beige powder (yield=44%).
M.p.=198-203° C.
$[\alpha]_D^{30}$=0° (c=0.18; DMSO).

EXAMPLE 133

5-(2-methoxyphenyl)-3-pyridinyl 5-thio-β-D-xylopyranoside

By following a procedure analogous to Example 122 starting from 2-methoxyphenylboronic acid and 5-bromo-3-pyridinyl 2,3,4-tri-O-acetyl-5-thio-β-D-xylopyranoside, 5-(2-methoxyphenyl)-3-pyridinyl 5-thio-β-D-xylopyranoside is obtained in the form of a beige powder (yield=69%).
M.p.=209-211° C.
$[\alpha]_D^{29}$=−94° (c=0.14; DMSO).

EXAMPLE 134

2-(4-methoxyphenyl)-6-methyl-3-pyridinyl 5-thio-β-D-xylopyranoside

By following a procedure analogous to Example 122 starting from 4-methoxyphenylboronic acid and the 2-iodo-6-methyl-3-pyridinyl 2,3,4-tri-O-acetyl-5-thio-β-D-xylopyranoside obtained according to Preparation 29, 2-(4-methoxyphenyl)-6-methyl-3-pyridinyl 5-thio-β-D-xylopyranoside is obtained in the form of an ecru powder (yield=70%).
M.p.=86-90° C.
$[\alpha]_D^{28}$=−25° (c=0.12; DMSO).

EXAMPLE 135

5-(4-chlorophenyl)-3-pyridinyl 5-thio-β-D-xylopyranoside

By following a procedure analogous to Example 122 starting from 4-chlorophenylboronic acid and 5-bromo-3-pyridinyl 2,3,4-tri-O-acetyl-5-thio-β-D-xylopyranoside, 5-(4-chlorophenyl)-3-pyridinyl 5-thio-β-D-xylopyranoside is obtained in the form of off-white crystals (yield=74%).
M.p.=202-203° C.
$[\alpha]_D^{29}$=−47° (c=0.48; DMSO).

EXAMPLE 136

5-(4-methoxy-3-methylphenyl)-3-pyridinyl 5-thio-β-D-xylopyranoside

By following a procedure analogous to Example 122 starting from 4-methoxy-3-methylphenylboronic acid and 5-bromo-3-pyridinyl 2,3,4-tri-O-acetyl-5-thio-β-D-xylopyranoside, 5-(4-methoxy-3-methylphenyl)-3-pyridinyl 5-thio-β-D-xylopyranoside is obtained in the form of a white solid (yield=21%).
M.p.=181° C.
$[\alpha]_D^{23}$=+55° (c=0.13; DMSO).

EXAMPLE 137

5-(2,4-dimethoxyphenyl)-3-pyridinyl 5-thio-α-D-xylopyranoside

By following a procedure analogous to Example 122 starting from 2,4-dimethoxyphenylboronic acid and 5-bromo-3-pyridinyl 2,3,4-tri-O-acetyl-5-thio-β-D-xylopyranoside, 5-(2,4-dimethoxyphenyl)-3-pyridinyl 5-thio-β-D-xylopyranoside is obtained in the form of a white solid (yield=71%).
M.p.=184° C.
$[\alpha]_D^{29}$=66° (c=0.1×DMSO).

EXAMPLE 138

5-(2-fluoro-5-methylphenyl)-3-pyridinyl 5-thio-β-D-xylopyranoside

By following a procedure analogous to Example 122 starting from 2-fluoro-5-methylphenylboronic acid and 5-bromo-3-pyridinyl 2,3,4-tri-O-acetyl-5-thio-β-D-xylopyranoside, 5-(2-fluoro-5-methylphenyl)-3-pyridinyl 5-thio-β-D-xylopyranoside is obtained in the form of white crystals (yield=48%).
M.p.=198° C. (crystallized from an ethanol/water mixture).
$[\alpha]_D^{30}$=−58° (c=0.18; DMSO).

EXAMPLE 139

5-(phenylsulfonyl)-3-pyridinyl 2,3,4-tri-O-acetyl-5-thio-β-D-xylopyranoside 0.495 g (1 mM) of 5-iodo-3-pyridinyl 2,3,4-tri-O-acetyl-5-thio-β-D-xylo-pyranoside, 4 ml of DMSO, 0.025 g (0.05 mM) of benzene/copper trifluoro-methanesulfonate complex, 0.196 g (1.2 mM) of phenyl sulfinate and 0.0088 g (0.1 mM) of N,N'-dimethylethylenediamine are mixed under an argon atmosphere in a reactor adapted for microwaves. The mixture is heated at 130° C. for 3 hours by microwaves. Water is added to the cooled reaction mixture and extraction is carried out with ethyl acetate. The organic phase is washed with water, dried over sodium sulfate, filtered and concentrated under reduced pressure. The evaporation residue is purified by chromatography on silica gel using a toluene/acetone mixture (9/1; v/v) as the eluent to give the expected product in the form of a white solid with a yield of 43%.
M.p.=97-99° C.
$[\alpha]_D^{30}$=−48° (c=0.17; DMSO).

EXAMPLE 140

5-(phenylsulfonyl)-3-pyridinyl 5-thio-β-D-xylopyranoside

By following a procedure analogous to Example 6 starting from the compound obtained in Example 139, 5-(phenylsulfonyl)-3-pyridinyl 5-thio-β-D-xylopyranoside is obtained in the form of a cottony white solid (yield=76%).
M.p.=86° C.
$[\alpha]_D^{29}$=−75° (c=0.20; DMSO).

EXAMPLE 141

5-[(4-fluorophenyl)sulfonyl]-3-pyridinyl 2,3,4-tri-O-acetyl-5-thio-β-D-xylo-pyranoside By following a procedure analogous to Example 139 starting from 5-iodo-3-pyridinyl 2,3,4-tri-O-acetyl-5-thio-β-D-xylopyranoside and 4-fluorophenyl sulfinate, 5-[(4-fluorophenyl)sulfonyl]-3-pyridinyl 2,3,4-tri-O-acetyl-5-thio-β-D-xylopyranoside is obtained in the form of a white solid (yield=24%).
M.p.=128° C.
$[\alpha]_D^{29}$=55° (c=0.26; DMSO).

EXAMPLE 142

5-[(4-fluorophenyl)sulfonyl]-3-pyridinyl 5-thio-β-D-xylopyranoside

By following a procedure analogous to Example 6 starting from the compound obtained in Example 141, 5-[(4-fluorophenyl)sulfonyl]-3-pyridinyl 5-thio-β-D-xylopyranoside is obtained in the form of a cottony white solid (yield=90%).
M.p.=93-96° C.
$[\alpha]_d^{29}$=−95° (c=0.20; DMSO).

EXAMPLE 143

5-(2,4,6-trifluorophenyl)-3-pyridinyl 2,3,4-tri-O-acetyl-5-thio-β-D-xylo-pyranoside 0.5 g (1.11 mM) of 5-bromo-3-pyridinyl 2,3,4-tri-O-acetyl-5-thio-β-D-xylo-pyranoside, 10 ml of DME, 0.027 g (0.033 mM) of [1,1-bis(diphenylphosphino)-ferrocene]dichloropalladium(II) dichloromethane, 0.564 g (2.23 mM) of bispinacolborane and 0.379 g (3.86 mM) of potassium acetate are mixed under an argon atmosphere in a reactor adapted for microwaves. The mixture is heated for 30 minutes at 110° C. by microwaves, cooled and filtered. 0.47 g (2.23 mM) of 2,4,6-trifluoro-1-bromobenzene, 0.091 g (0.11 mM) of [1,1'-bis(diphenylphosphino)ferrocene]dichloropalladium (II) dichloromethane and a solution of 0.177 g (1.67 mM) of sodium carbonate in 1 ml of water are added to the filtrate. The reaction mixture is heated for 30 minutes at 130° C. in a microwave oven. Water is added to the cooled medium and extraction is carried out with ethyl acetate. The organic phase is washed with aqueous sodium bicarbonate solution and then with water, dried over sodium sulfate and concentrated under reduced pressure. The evaporation residue is purified by chromatography on silica gel using a cyclohexane/ethyl acetate mixture (8/2; v/v) as the eluent to give the desired product in the form of a white solid with a yield of 39%.
M.p.=143° C.
$[\alpha]_d^{27}$=−21° (c=0.20; DMSO).

EXAMPLE 144

5-(2,4,6-trifluorophenyl)-3-pyridinyl 5-thio-β-D-xylopyranoside

By following a procedure analogous to Example 6 starting from the compound obtained in Example 143, 5-(2,4,6-trifluorophenyl)-3-pyridinyl 5-thio-β-D-xylopyranoside is obtained in the form of a white solid (yield=56%).
M.p. 228° C.
$[\alpha]_d^{28}$=−63° (c=0.22; DMSO).

EXAMPLE 145

5-(3,5-difluoro-4-methoxyphenyl)-3-pyridinyl 2,3,4-tri-O-acetyl-5-thio-β-D-xylopyranoside 0.334 g (1.5 mM) of 4-bromo-2,6-difluoroanisole, 12 ml of DME, 0.569 g (2.25 mM) of bispinacolborane, 0.036 g (0.045 mM) of [1,1'-bis(diphenyl-phosphino)ferrocene]dichloropalladium(II) dichloromethane and 0.441 g (4.5 mM) of potassium acetate are mixed in a reactor adapted for microwaves. The reactor is heated at 110° C. for 30 minutes by microwaves. After cooling, the reaction mixture is filtered and 0.672 g (1.8 mM) of 5-bromo-3-pyridinyl 2,3,4-tri-O-acetyl-5-thio-β-D-xylopyranoside, 1.122 g (0.12 mM) of [1,1'-bis(diphenylphosphino)ferrocene]dichloropalladium (II) dichloromethane and a solution of 0.196 g (1.8 mM) of sodium carbonate in 1.5 ml of water are then added to the filtrate. The mixture is heated at 130° C. for 30 minutes by microwaves. Water is added to the cooled reaction mixture and extraction is carried out with ethyl acetate. The organic phase is washed with water, dried over sodium sulfate, filtered and concentrated under reduced pressure. The evaporation residue is purified by chromatography on silica gel using a dichloromethane/methanol mixture (99/1; v/v) as the eluent. The product obtained is recrystallized from ether and filtered off to give the desired product in the form of a white powder with a yield of 64%.
M.p.=203° C.
$[\alpha]_d^{29}$=−18° (c=0.30; DMSO).

EXAMPLE 146

5-(3,5-difluoro-4-methoxyphenyl)-3-pyridinyl 5-thio-β-D-xylopyranoside

By following a procedure analogous to Example 6 starting from the compound obtained in Example 145, 5-(3,5-difluoro-4-methoxyphenyl)-3-pyridinyl 5-thio-β-D-xylopyranoside is obtained in the form of a white powder (yield=74%).
M.p.=203° C.
$[\alpha]_D^{29}$=64° (c=0.35; DMSO).

EXAMPLE 147

5-(2-cyano-4-fluorophenyl)-3-pyridinyl 2,3,4-tri-O-acetyl-5-thio-β-D-xylo-pyranoside By following a procedure analogous to Example 145 starting from 2-bromo-5-fluorobenzonitrile, 5-(2-cyano-4-fluorophenyl)-3-pyridinyl 2,3,4-tri-O-acetyl-5-thio-β-D-xylopyranoside is obtained in the form of a cream-colored solid (yield=29%).
M.p.=170-172° C.
$[\alpha]_D^{23}$=−23° (c=0.14; DMSO).

EXAMPLE 148

5-(2-cyano-4-fluorophenyl)-3-pyridinyl 5-thio-β-D-xylopyranoside

By following a procedure analogous to Example 2 starting from the compound obtained in Example 147, 5-(2-cyano-4-fluorophenyl)-3-pyridinyl 5-thio-β-D-xylopyranoside is obtained in the form of a beige solid (yield=70%).
M.p.=198-200° C. (crystallized from diethyl ether).
$[\alpha]_D^{23}$=−70° (c=0.20; DMSO).

EXAMPLE 149

5-(4-cyano-3-methylphenyl)-3-pyridinyl 2,3,4-tri-O-acetyl-5-thio-β-D-xylo-pyranoside By following a procedure analogous to Example 145 starting from 4-bromo-2-methylbenzonitrile, 5-(4-cyano-3-methylphenyl)-3-pyridinyl 2,3,4-tri-O-acetyl-5-thio-β-D-xylopyranoside is obtained in the form of an off-white solid (yield=61%).
M.p.=74-80° C.
$[\alpha]_D^{23}$=−15° (c=0.16; DMSO).

EXAMPLE 150

5-(4-cyano-3-methylphenyl)-3-pyridinyl 5-thio-β-D-xylopyranoside

By following a procedure analogous to Example 2 starting from the compound obtained in Example 149, 5-(4-cyano-3- methylphenyl)-3-pyridinyl 5-thio-β-D-xylopyranoside is obtained in the form of white crystals (yield=79%).
M.p.=198-200° C.
$[\alpha]_D^{23}$=−72° (c=0.25; DMSO).

EXAMPLE 151

5-(3-chloro-4-cyanophenyl)-3-pyridinyl 2,3,4-tri-O-acetyl-5-thio-β-D-xylo-pyranoside By following a procedure analogous to Example 145 starting from 4-bromo-2-chlorobenzonitrile, 5-(3-chloro-4-cyanophenyl)-3-pyridinyl 2,3,4-tri-O-acetyl-5-thio-β-D-xylopyranoside is obtained in the form of white crystals (yield=39%).
M.p.=148-150° C. (crystallized from ethyl acetate).
$[\alpha]_D^{24}$=6° (c=0.16; DMSO).

EXAMPLE 152

5-(3-chloro-4-cyanophenyl)-3-pyridinyl 5-thio-β-D-xylopyranoside

By following a procedure analogous to Example 2 starting from the compound obtained in Example 151, 5-(3-chloro-4-cyanophenyl)-3-pyridinyl 5-thio-β-D-xylopyranoside is obtained in the form of a white solid (yield=35%).
M.p.=202-204° C.
$[\alpha]_D^{25}$=−73° (c=0.10; DMSO).

EXAMPLE 153

5-(4-cyano-2-methylphenyl)-3-pyridinyl 2,3,4-tri-O-acetyl-5-thio-β-D-xylo-pyranoside By following a procedure analogous to Example 145 starting from 4-bromo-3-methylbenzonitrile, 5-(4-cyano-2-methylphenyl)-3-pyridinyl 2,3,4-tri-O-acetyl-5-thio-β-D-xylopyranoside is obtained in the form of off-white crystals (yield=54%).
M.p.=136-138° C. (crystallized from diethyl ether).
$[\alpha]_D^{25}$=−7° (c=0.18; DMSO).

EXAMPLE 154

5-(4-cyano-2-methylphenyl)-3-pyridinyl 5-thio-β-D-xylopyranoside

By following a procedure analogous to Example 2 starting from the compound obtained in Example 153, 5-(4-cyano-2-methylphenyl)-3-pyridinyl 5-thio-β-D-xylopyranoside is obtained in the form of white crystals (yield=73%).
M.p.=202-206° C.
$[\alpha]_D^{25}$=−62° (c=0.17; DMSO).

EXAMPLE 155

5-(3,4-dicyanophenyl)-3-pyridinyl 2,3,4-tri-O-acetyl-5-thio-β-D-xylo-pyranoside

By following a procedure analogous to Example 145 starting from 4-iodo-1,2-benzenedicarbonitrile, 5-(3,4-dicyanophenyl)-3-pyridinyl 2,3,4-tri-O-acetyl-5-thio-β-D-xylopyranoside is obtained in the form of white crystals (yield=45%).
M.p.=114° C.
$[\alpha]_D^{28}$=−11° (c=0.39; DMSO).

EXAMPLE 156

5-(3,4-dicyanophenyl)-3-pyridinyl 5-thio-β-D-xylopyranoside

By following a procedure analogous to Example 6 starting from the compound obtained in Example 155, 5-(3,4-dicyanophenyl)-3-pyridinyl 5-thio-β-D-xylopyranoside is obtained in the form of white crystals (yield=19%).
M.p.=192° C. (crystallized from methanol).
$[\alpha]_D^{28}$=−43° (c=0.20; DMSO).

EXAMPLE 157

6-[4-(1-piperidinyl)phenyl]-3-pyridinyl 2,3,4-tri-O-acetyl-5-thio-β-D-xylo-pyranoside By following a procedure analogous to Example 43 starting from [4-(1-piperidinyl)phenyl]boronic acid and 6-bromo-3-pyridinyl 2,3,4-tri-O-acetyl-5-thio-β-D-xylopyranoside, the expected compound is obtained in the form of a gray powder (yield=14%).
M.p.=212° C.
$[\alpha]_D^{28}$=+14° (c=0.12; DMSO).

EXAMPLE 158

6-[4-(1-piperidinyl)phenyl]-3-pyridinyl 5-thio-β-D-xylopyranoside

By following a procedure analogous to Example 6 starting from the product obtained in Example 157, 6-[4-(1-piperidinyl)phenyl]-3-pyridinyl 5-thio-β-D-xylo-pyranoside is obtained in the form of a white solid with a yield of 72%.
M.p.=221° C.
$[\alpha]_D^{26}$=−15° (c=0.13; DMSO).

EXAMPLE 159

5-[(N,N-diethylamino)carbonyl]-3-pyridinyl 2,3,4-tri-O-acetyl-5-thio-β-D-xylopyranoside A procedure analogous to the first part of Example 143 is followed starting from 5-bromo-3-pyridinyl 2,3,4-tri-O-acetyl-5-thio-β-D-xylopyranoside and bis-pinacolborane. After filtration and evaporation of the reaction mixture, the residue is extracted with ethyl acetate and washed with water. The organic phase is dried over magnesium sulfate and then concentrated under reduced pressure to give a brown oil which, when triturated in an ethyl ether/diisopropyl ether mixture, gives 5-(4,4,5,5-tetramethyl-1,3,2-dioxaborolan-2-yl)-3-pyridinyl 2,3,4-tri-O-acetyl-5-thio-β-D-xylopyranoside. The product obtained is used directly in the next step.

1 g (2.02 mM) of 5-(4,4,5,5-tetramethyl-1,3,2-dioxaborolan-2-yl)-3-pyridinyl 2,3,4-tri-O-acetyl-5-thio-β-D-xylopyranoside, 0.5 ml (3.95 mM) of diethylcarbamoyl chloride, 50 mg (0.06 mM) of [1,1′-bis(diphenylphosphino)-ferrocene] dichloropalladium(II) dichloromethane and 15 ml of THF are placed under an argon atmosphere in a reactor adapted for microwaves. The mixture is heated at 110° C. for 30 minutes by microwaves. The cooled reaction mixture is filtered and then concentrated under reduced pressure. The evaporation residue is purified by chromatography on silica gel using pure dichloromethane and then a dichloromethane/methanol mixture (9/1; v/v) as the eluent. After washing with an ether/isopropyl ether mixture, the brown solid obtained is used directly in the deacetylation reaction described in Example 160.

EXAMPLE 160

5-[(N,N-diethylamino)carbonyl]-3-pyridinyl 5-thio-β-D-xylopyranoside

By following a procedure analogous to Example 6 starting from the product obtained in Example 159, 5-[(N,N-diethylamino)carbonyl]-3-pyridinyl 5-thio-β-D-xylopyranoside is obtained in the form of a beige solid with a yield of 59%.
M.p.=143° C. (crystallized from water).
$[\alpha]_D^{25}$=−53° (c=0.11; DMSO).

EXAMPLE 161

2-(4-fluoro-2-methylphenyl)-4-pyridinyl 2,3,4-tri-O-acetyl-5-thio-β-D-xylo-pyranoside By following a procedure analogous to Example 76 starting from 4-fluoro-2-methylphenylboronic acid, 2-(4-fluoro-2-methylphenyl)-4-pyridinyl 2,3,4-tri-O-acetyl-5-thio-β-D-xylopyranoside is obtained in the form of a white solid with a yield of 72%.

M.p.=137° C.

$[\alpha]_D^{29}$=−14° (c=0.28; DMSO).

EXAMPLE 162

2-(4-fluoro-2-methylphenyl)-4-pyridinyl 5-thio-β-D-xylopyranoside

By following a procedure analogous to Example 6 starting from the product obtained in Example 161, 2-(4-fluoro-2-methylphenyl)-4-pyridinyl 5-thio-β-D-xylopyranoside is obtained in the form of a white solid with a yield of 70%.

M.p.=147° C. (crystallized from a water/DMSO mixture).

$[\alpha]_D^{32}$=−52° (c=0.20; DMSO).

The structures of the compounds of formula I described above are summarized in the Table below:

| Ex. | Position of N | X | Ra | R₂ | R |
|---|---|---|---|---|---|
| 1 | 3 |  | 6-acetyl | H | Ac |
| 2 | 3 |  | 6-acetyl | H | H |
| 3 | 3 |  | 2-acetyl | H | Ac |
| 4 | 3 |  | 2-acetyl | H | H |
| 5 | 3 | 2-CO | 4-cyanophenyl | H | Ac |
| 6 | 3 | 2-CO | 4-cyanophenyl | H | H |
| 7 | 3 | 6-CO | 4-(trifluoromethyl)phenyl | H | Ac |
| 8 | 3 | 6-CO | 4-(trifluoromethyl)phenyl | H | H |
| 9 | 3 | 6-sb | 4-cyanophenyl | H | Ac |
| 10 | 3 | 6-sb | 4-cyanophenyl | H | H |
| 11 | 3 | 2-sb | 4-cyanophenyl | H | Ac |
| 12 | 3 | 2-sb | 4-cyanophenyl | H | H |
| 13 | 3 | 5-sb | phenyl | H | Ac |
| 14 | 3 | 5-sb | phenyl | H | H |
| 15 | 3 | 5-sb | 4-cyanophenyl | H | Ac |
| 16 | 3 | 5-sb | 4-cyanophenyl | H | H |
| 17 | 3 | 6-SO₂ | 4-cyanophenyl | H | Ac |
| 18 | 3 | 6-SO₂ | 4-cyanophenyl | H | H |
| 19 | 3 |  | 2-methylsulfonyl | H | Ac |
| 20 | 3 |  | 2-methylsulfonyl | H | H |
| 21 | 3 |  | 6-methylsulfonyl | H | Ac |
| 22 | 3 |  | 6-methylsulfonyl | H | H |
| 23 | 3 | 2-sb | phenyl | H | Ac |
| 24 | 3 | 2-sb | phenyl | H | H |
| 25 | 3 | 5-O | phenyl | H | Ac |
| 26 | 3 | 5-O | phenyl | H | H |
| 27 | 3 | 4-sb | 4-cyanophenyl | H | Ac |
| 28 | 3 | 4-sb | 4-cyanophenyl | H | H |
| 29 | 3 | 5-CO | benzylamino | H | H |
| 30 | 3 | 6-sb | phenyl | 5-F | Ac |
| 31 | 3 | 6-sb | phenyl | 5-F | H |
| 32 | 3 | 5-sb | 4-cyanophenyl | 2-F | Ac |
| 33 | 3 | 5-sb | 4-cyanophenyl | 2-F | H |
| 34 | 3 | 4-sb | trifluoromethylphenyl | H | Ac |
| 35 | 3 | 4-sb | trifluoromethylphenyl | H | H |
| 36 | 3 | 5-sb | 4-(trifluoromethoxy)phenyl | H | H |
| 37 | 3 | 5-sb | 3-acetylphenyl | H | H |
| 38 | 3 | 5-sb | 4-fluorophenyl | H | H |
| 39 | 3 |  | 2-(1-piperidinyl)carbonyl | H | Ac |
| 40 | 3 |  | 2-(1-piperidinyl)carbonyl | H | H |
| 41 | 3 |  | 2-(dimethylaminocarbonyl) | H | Ac |
| 42 | 3 |  | 2-(dimethylaminocarbonyl) | H | H |
| 43 | 3 | 5-sb | 4-methoxyphenyl | H | Ac |
| 44 | 3 | 5-sb | 4-methoxyphenyl | H | H |
| 45 | 3 | 5-sb | 4-(hydroxymethyl)phenyl | H | Ac |
| 46 | 3 | 5-sb | 4-(hydroxymethyl)phenyl | H | H |

-continued

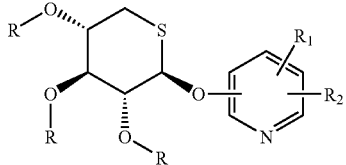

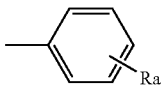

| Ex. | Position of N | X | R₁ | R₂ | R |
|---|---|---|---|---|---|
| 47 | 3 | 5-sb | 4-(1-piperidinyl)phenyl | H | Ac |
| 48 | 3 | 5-sb | 4-(1-piperidinyl)phenyl | H | H |
| 49 | 3 | 5-sb | 4-(dimethylamino)phenyl | H | Ac |
| 50 | 3 | 5-sb | 4-(dimethylamino)phenyl | H | H |
| 51 | 3 | 5-sb | 4-methylphenyl | H | Ac |
| 52 | 3 | 5-sb | 4-methylphenyl | H | H |
| 53 | 3 | 5-sb | 4-(trifluoromethyl)phenyl | H | Ac |
| 53' | 3 | 5-sb | 4-(trifluoromethyl)phenyl | H | H |
| 54 | 3 | 5-sb | 3-cyanophenyl | H | Ac |
| 55 | 3 | 5-sb | 3-cyanophenyl | H | H |
| 56 | 3 | 4-sb | 4-fluorophenyl | H | Ac |
| 57 | 3 | 4-sb | 4-fluorophenyl | H | H |
| 58 | 3 | 5-sb | 4-fluoro-3-methylphenyl | H | Ac |
| 59 | 3 | 5-sb | 4-fluoro-3-methylphenyl | H | H |
| 60 | 3 | 5-sb | 4-fluoro-2-methylphenyl | H | Ac |
| 61 | 3 | 5-sb | 4-fluoro-2-methylphenyl | H | H |
| 62 | 3 | 5-sb | 3-cyano-4-fluorophenyl | H | Ac |
| 63 | 3 | 5-sb | 3-cyano-4-fluorophenyl | H | H |
| 64 | 3 | 5-sb | 3-chloro-4-methoxyphenyl | H | Ac |
| 65 | 3 | 5-sb | 3-chloro-4-methoxyphenyl | H | H |
| 66 | 3 | 5-sb | 3-methoxyphenyl | H | Ac |
| 67 | 3 | 5-sb | 3-methoxyphenyl | H | H |
| 68 | 3 | 5-sb | 4-(1-methylethoxy)phenyl | H | Ac |
| 69 | 3 | 5-sb | 4-(1-methylethoxy)phenyl | H | H |
| 70 | 3 | 5-sb | 3,4-dimethoxyphenyl | H | Ac |
| 71 | 3 | 5-sb | 3,4-dimethoxyphenyl | H | H |
| 72 | 3 | 2-sb | 4-fluorophenyl | H | Ac |
| 73 | 3 | 2-sb | 4-fluorophenyl | H | H |
| 74 | 3 | 2-sb | 4-methoxyphenyl | 4-methyl | Ac |
| 75 | 3 | 2-sb | 4-methoxyphenyl | 4-methyl | H |
| 76 | 4 | 2-sb | 4-methoxyphenyl | H | Ac |
| 77 | 4 | 2-sb | 4-methoxyphenyl | H | H |
| 78 | 3 | 5-sb | 3-fluoro-4-(1-methylethoxy)phenyl | H | Ac |
| 79 | 3 | 5-sb | 3-fluoro-4-(1-methylethoxy)phenyl | H | H |
| 80 | 3 | 5-sb | 2,6-difluoro-4-methoxyphenyl | H | Ac |
| 81 | 3 | 5-sb | 2,6-difluoro-4-methoxyphenyl | H | H |
| 82 | 3 | 5-sb | 3,5-dimethyl-4-methoxyphenyl | H | Ac |
| 83 | 3 | 5-sb | 3,5-dimethyl-4-methoxyphenyl | H | H |
| 84 | 3 | 5-sb | 2,4-difluorophenyl | H | Ac |
| 85 | 3 | 5-sb | 2,4-difluorophenyl | H | H |
| 86 | 3 | 5-sb | 4-fluoro-2-methoxyphenyl | H | Ac |
| 87 | 3 | 5-sb | 4-fluoro-2-methoxyphenyl | H | H |
| 88 | 3 | 5-sb | 2-chloro-4-fluorophenyl | H | Ac |
| 89 | 3 | 5-sb | 2-chloro-4-fluorophenyl | H | H |
| 90 | 3 | 5-sb | 4-cyano-3-fluorophenyl | H | Ac |
| 91 | 3 | 5-sb | 4-cyano-3-fluorophenyl | H | H |
| 92 | 3 | 6-sb | 4-methoxyphenyl | H | Ac |
| 93 | 3 | 6-sb | 4-methoxyphenyl | H | H |
| 94 | 3 | 6-sb | 4-hydroxymethylphenyl | H | Ac |
| 95 | 3 | 6-sb | 4-hydroxymethylphenyl | H | H |
| 96 | 3 | 6-sb | 4-trifluoromethylphenyl | H | Ac |
| 97 | 3 | 6-sb | 4-trifluoromethylphenyl | H | H |
| 98 | 3 | 6-sb | 4-methylphenyl | H | Ac |
| 99 | 3 | 6-sb | 4-methylphenyl | H | H |
| 100 | 3 | 4-sb | 4-methoxyphenyl | H | Ac |
| 101 | 3 | 4-sb | 4-methoxyphenyl | H | H |
| 102 | 3 | 5-sb | 3-fluoro-4-methoxyphenyl | H | Ac |
| 103 | 3 | 5-sb | 3-fluoro-4-methoxyphenyl | H | H |
| 104 | 3 | 5-sb | 4-methoxy-2-methylphenyl | H | Ac |
| 105 | 3 | 5-sb | 4-methoxy-2-methylphenyl | H | H |
| 106 | 3 | 5-sb | 3-fluoro-4-methylphenyl | H | Ac |
| 107 | 3 | 5-sb | 3-fluoro-4-methylphenyl | H | H |
| 108 | 3 | 5-sb | 3,4-dimethylphenyl | H | Ac |

-continued

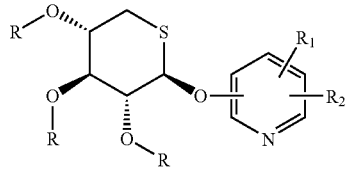

(I)

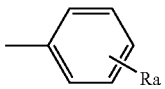

| Ex. | Position of N | X | R₁ | R₂ | R |
|---|---|---|---|---|---|
| 109 | 3 | 5-sb | 3,4-dimethylphenyl | H | H |
| 110 | 3 | 5-sb | 2-chloro-4-methylphenyl | H | Ac |
| 111 | 3 | 5-sb | 2-chloro-4-methylphenyl | H | H |
| 112 | 3 | 5-sb | 2-chloro-4-methoxyphenyl | H | Ac |
| 113 | 3 | 5-sb | 2-chloro-4-methoxyphenyl | H | H |
| 114 | 3 | | 5-methylsulfonyl | H | Ac |
| 115 | 3 | | 5-methylsulfonyl | H | H |
| 116 | 3 | | 6-[(phenylmethyl)amino]carbonyl | H | Ac |
| 117 | 3 | | 6-[(phenylmethyl)amino]carbonyl | H | H |
| 118 | 3 | | 5-acetyl | H | Ac |
| 119 | 3 | | 5-acetyl | H | H |
| 120 | 3 | | 4-acetyl | H | Ac |
| 121 | 3 | | 4-acetyl | H | H |
| 122 | 3 | 2-sb | 4-methoxyphenyl | H | H |
| 123 | 3 | 5-sb | 3-fluorophenyl | H | H |
| 124 | 3 | 6-sb | 3-acetylphenyl | H | H |
| 125 | 3 | 6-sb | 4-(trifluoromethoxy)phenyl | H | H |
| 126 | 3 | 5-sb | 2-fluorophenyl | H | H |
| 127 | 3 | 2-sb | 4-(trifluoromethoxy)phenyl | H | H |
| 128 | 3 | 2-sb | 3-acetylphenyl | H | H |
| 129 | 3 | 6-sb | 4-fluorophenyl | H | H |
| 130 | 3 | 5-sb | 2-cyanophenyl | H | H |
| 131 | 3 | 5-sb | 3-chloro-4-fluorophenyl | H | H |
| 132 | 3 | 5-sb | 3,4-difluorophenyl | H | H |
| 133 | 3 | 5-sb | 2-methoxyphenyl | H | H |
| 134 | 3 | 2-sb | 4-methoxyphenyl | 6-methyl | H |
| 135 | 3 | 5-sb | 4-chlorophenyl | H | H |
| 136 | 3 | 5-sb | 4-methoxy-3-methylphenyl | H | H |
| 137 | 3 | 5-sb | 2,4-dimethoxyphenyl | H | H |
| 138 | 3 | 5-sb | 2-fluoro-5-methylphenyl | H | H |
| 139 | 3 | 5-SO₂ | phenyl | H | Ac |
| 140 | 3 | 5-SO₂ | phenyl | H | H |
| 141 | 3 | 5-SO₂ | 4-fluorophenyl | H | Ac |
| 142 | 3 | 5-SO₂ | 4-fluorophenyl | H | H |
| 143 | 3 | 5-sb | 2,4,6-trifluorophenyl | H | Ac |
| 144 | 3 | 5-sb | 2,4,6-trifluorophenyl | H | H |
| 145 | 3 | 5-sb | 3,5-difluoro-4-methoxyphenyl | H | Ac |
| 146 | 3 | 5-sb | 3,5-difluoro-4-methoxyphenyl | H | H |
| 147 | 3 | 5-sb | 2-cyano-4-fluorophenyl | H | Ac |
| 148 | 3 | 5-sb | 2-cyano-4-fluorophenyl | H | H |
| 149 | 3 | 5-sb | 4-cyano-3-methylphenyl | H | Ac |
| 150 | 3 | 5-sb | 4-cyano-3-methylphenyl | H | H |
| 151 | 3 | 5-sb | 3-chloro-4-cyanophenyl | H | Ac |
| 152 | 3 | 5-sb | 3-chloro-4-cyanophenyl | H | H |
| 153 | 3 | 5-sb | 4-cyano-2-methylphenyl | H | Ac |
| 154 | 3 | 5-sb | 4-cyano-2-methylphenyl | H | H |
| 155 | 3 | 5-sb | 3,4-dicyanophenyl | H | Ac |
| 156 | 3 | 5-sb | 3,4-dicyanophenyl | H | H |
| 157 | 3 | 6-sb | 4-(1-piperidinyl)phenyl | H | Ac |
| 158 | 3 | 6-sb | 4-(1-piperidinyl)phenyl | H | H |
| 159 | 3 | | 5-[(N,N-diethylamino)carbonyl] | H | Ac |
| 160 | 3 | | 5-[(N,N-diethylamino)carbonyl] | H | H |
| 161 | 4 | 2-sb | 4-fluoro-2-methylphenyl | H | Ac |
| 162 | 4 | 2-sb | 4-fluoro-2-methylphenyl | H | H |

Ac = COCH₃
sb = carbon-carbon single bond

The antithrombotic activity of the compounds according to the invention was studied in vivo in the rat by means of a test that reproduces a venous thrombosis.

The venous thrombosis was induced according to the protocol described in *Thromb. Haemost.*, 1992, 67(1), 176-179. The oral activity was studied according to the following operating protocol:

The experiments are performed on non-fasted Wistar male rats weighing 250 to 280 g, divided into groups of 10 animals each. The test products are administered orally (tubage) dissolved or suspended in a solution of methyl cellulose (0.5% in water). The concentration of the compounds is calculated so that the amount of solution absorbed is 10 ml/kg by oral administration. A thrombosis is induced at a time T (2 or 8 hours) after administration of the product, and the thrombus formed is removed and weighed. To induce this thrombosis, a venous stasis is created under hypercoagulation according to the technique described by WESSLER (*J. Applied Physiol.*, 1959, 943-946), the hypercoagulating agent used being a solution of activated factor X (Xa) having a concentration of 7.5 nKat/kg, supplied by Biogenic (Montpellier). The venous stasis is effected exactly 10 seconds after injection of the hypercoagulating agent. The activity of the test compounds was checked at different doses after they had been administered. The thrombosis was induced 2 hours or 8 hours after administration of the compound. By way of example, the results of the above tests are shown in the Table below for a few compounds according to the invention (the activity is expressed as the percentage inhibition of thrombus formation observed in the presence of the compound according to the invention, relative to the weight of the thrombus formed in the absence of the compound).

TABLE I

Oral activity

| Example | Dose (mg/kg) | Time (h) | Activity (%) |
|---|---|---|---|
| 2 | 6 | 2 | 63 |
| 3 | 8.6 | 2 | 92 |
| 4 | 6 | 2 | 96 |
| 6 | 6 | 2 | 61 |
| 6 | 6 | 8 | 26 |
| 8 | 6 | 2 | 46 |
| 12 | 6 | 2 | 14 |
| 14 | 6 | 2 | 50 |
| 15 | 8.2 | 2 | 84 |
| 59 | 6 | 2 | 82 |
| 61 | 6 | 2 | 98 |
| 89 | 6 | 2 | 100 |
| 99 | 6 | 2 | 72 |
| 101 | 6 | 2 | 97 |
| 103 | 6 | 2 | 100 |
| 123 | 6 | 2 | 97 |
| 126 | 6 | 2 | 91 |
| 131 | 6 | 2 | 80 |

These results show that the compounds according to the invention exhibit a venous antithrombotic activity.

The present invention therefore relates to a compound of formula (I) according to the invention, and its pharmaceutically acceptable salts with an acid, solvates and hydrates, for use as drugs. The compound of formula (I), or one of its pharmaceutically acceptable salts, solvates or hydrates, may be used for the preparation of an antithrombotic drug intended in particular for the treatment or prevention of disorders of the venous circulation and especially for correcting certain hematological parameters perceptible in the venous system or for compensating a cardiac insufficiency.

The present invention therefore further relates to pharmaceutical compositions containing a compound of formula (I) or one of its pharmaceutically acceptable salts, solvates or hydrates. These pharmaceutical compositions generally contain suitable excipients. Said excipients are chosen according to the desired pharmaceutical form and the desired mode of administration, particularly oral administration or administration by injection.

These pharmaceutical compositions are prepared by the conventional methods well known to those skilled in the art. For example, the compounds according to the invention can be formulated with physiologically acceptable excipients to give an injectable form for direct use, an injectable form to be prepared immediately before use, or a solid form for oral administration, e.g. a capsule or a tablet.

By way of example, an injectable form can preferably be prepared by the lyophilization of a sterilized filtered solution containing the compound according to the invention and a soluble excipient in a necessary and sufficient amount to give an isotonic solution after the addition of injectable water immediately before use. The resulting solution may be administered either in a single subcutaneous or intramuscular injection or in the form of a slow perfusion. A form for oral administration will preferably be presented in the form of a capsule containing the finely ground or, preferably, micronized compound of the invention mixed with excipients known to those skilled in the art, e.g. lactose, pregelatinized starch and magnesium stearate.

To obtain the desired therapeutic or prophylactic effect, each unit dose can contain 10 to 500 mg of at least one compound according to the invention.

What is claimed is:
1. A compound selected from the group consisting of:
a) compounds corresponding to formula I

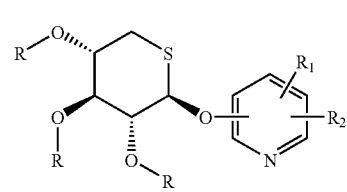

wherein
the pentapyranosyl group is a free or acylated 5-thio-β-D-xylopyranosyl group;
R is a hydrogen atom or a $C_2$-$C_6$ acyl group;
$R_1$ is a $C_1$-$C_4$ alkylsulfonyl group, a $C_2$-$C_6$ acyl group, a group CONR'R" or a group

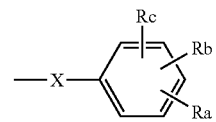

wherein
X is a single bond, an oxygen atom, a sulfoxy group, a group —CO— or a group —CHOH—;
Ra is a hydrogen atom, a halogen, a hydroxyl group, a $C_1$-$C_4$ alkyl group, a trifluoromethyl group, a trifluoromethoxy group, a cyano group, a $C_1$-$C_4$ hydroxyalkyl group, a $C_2$-$C_4$ acyl group, a $C_1$-$C_4$ alkoxy group or a group NR'R";

wherein R' and R" independently are each a hydrogen atom or a $C_1$-$C_4$ alkyl group optionally substituted by an aromatic ring, or together with the nitrogen atom to which they are attached form a ring having 5 or 6 carbon atoms;

Rb and Rc independently of one another are each a hydrogen atom, a halogen atom, a $C_1$-$C_4$ alkyl group, a cyano group or a $C_1$-$C_4$ alkoxy group; and $R_2$ is a hydrogen atom, a $C_1$-$C_4$ alkyl group or a halogen atom;

b) acid addition salts of a); and c) active metabolites of b) and c).

2. A compound according to claim 1, wherein $R_1$ is a group corresponding to the formula:

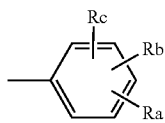

wherein Ra, Rb and Rc are as defined in claim 1.

3. A compound according to claim 1, wherein R is a hydrogen atom.

4. A compound according to claim 1, wherein R is $COCH_3$.

5. A process for producing a compound according to claim 1, said process comprising:

a) reacting a pyridinol corresponding to formula II

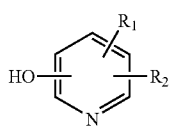

wherein $R_1$ is a $C_1$-$C_4$ alkylsulfonyl group, a $C_2$-$C_6$ acyl group, a group $CONR'R''$ or a group

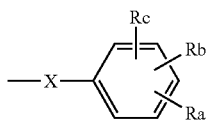

wherein

X is a single bond, an oxygen atom, a sulfoxy group, a group —CO— or a group —CHOH—;

Ra is a hydrogen atom, a halogen, a $C_1$-$C_4$ alkyl group, a trifluoromethyl group, a trifluoromethoxy group, a cyano group, a $C_1$-$C_4$ hydroxyalkyl group, a $C_2$-$C_4$ acyl group, a $C_1$-$C_4$ alkoxy group or a group $NR'R''$;

wherein R' and R" independently are each a hydrogen atom or a $C_1$-$C_4$ alkyl group optionally substituted by an aromatic ring, or together with the nitrogen atom to which they are attached form a ring having 5 or 6 carbon atoms, Rb and Rc independently of one another are each a hydrogen atom, a halogen atom, a $C_1$-$C_4$ alkyl group, a cyano group or a $C_1$-$C_4$ alkoxy group, and $R_2$ is a hydrogen atom, a $C_1$-$C_4$ alkyl group or a halogen atom, with a 5-thioxylopyranose compound corresponding to formula III-D

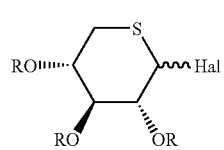

wherein

Hal is a halogen, and

R is a $C_2$-$C_6$ acyl group, in an aprotic solvent, in the presence of a silver salt or a zinc salt, in an anhydrous medium, at a temperature between 25 and 110° C., for 1 to 10 hours, to yield a compound corresponding to formula I

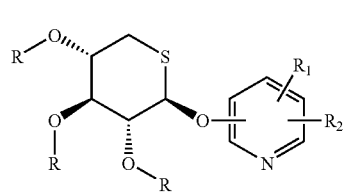

wherein R, $R_1$ and $R_2$ have the meanings given above;

b) optionally reacting the compound of formula I obtained in a) with a solution of ammonia in methanol to yield a compound corresponding to formula Ia

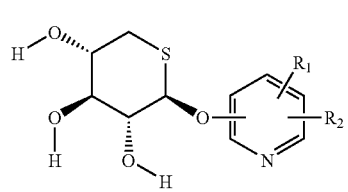

wherein $R_1$ and $R_2$ have the meanings given above, and c) optionally reacting the compound of formula I obtained in a) or the compound of formula Ia obtained in b) with an acid to yield a corresponding acid addition salt.

6. A process according to claim 5, wherein Hal is bromine.

7. A process for producing a compound according to claim 1, said process comprising:

a) reacting tetra-O-acetyl-5-thioxylopyranose corresponding to formula IV-D

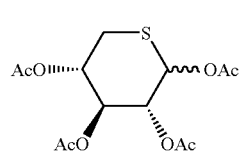

wherein Ac is an acetyl group, with a compound corresponding to formula II

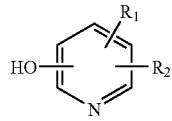

wherein
R$_1$ is a C$_1$-C$_4$ alkylsulfonyl group, a C$_2$-C$_6$ acyl group, a group CONR'R" or a group

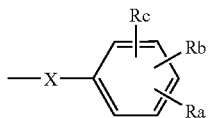

wherein
X is a single bond, an oxygen atom, a sulfoxy group, a group —CO— or a group —CHOH—,
Ra is a hydrogen atom, a halogen, a C$_1$-C$_4$ alkyl group, a trifluoromethyl group, a trifluoromethoxy group, a cyano group, a C$_1$-C$_4$ hydroxyalkyl group, a C$_2$-C$_4$ acyl group, a C$_1$-C$_4$ alkoxy group or a group NR'R",
wherein R' and R" independently are each a hydrogen atom or a C$_1$-C$_4$ alkyl group optionally substituted by an aromatic ring, or form, together with the nitrogen atom to which they are attached, a ring having 5 or 6 carbon atoms,
Rb and Rc independently of one another are each a hydrogen atom, a halogen atom, a C$_1$-C$_4$ alkyl group, a cyano group or a C$_1$-C$_4$ alkoxy group, and
R$_2$ is a hydrogen atom, a C$_1$-C$_4$ alkyl group or a halogen atom, in an aprotic solvent, in the presence of a Lewis acid catalyst, at a temperature between 20 and 60° C., for 1 to 2 hours, to yield a compound corresponding to formula Ib

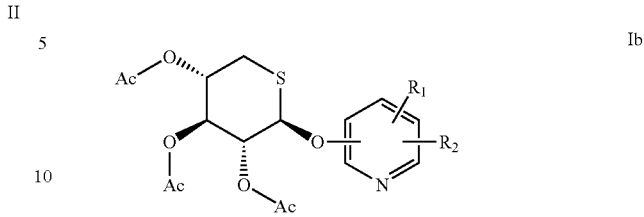

wherein R$_1$ and R$_2$ have the meanings given above;
b) optionally reacting the compound of formula I obtained in a) with sodium methylate in methanol to yield a compound corresponding to formula Ia

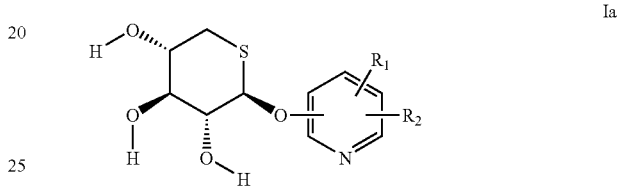

wherein R$_1$ and R$_2$ have the meanings given above, and
c) optionally reacting the compound of formula Ib obtained in a) or the compound of formula Ia obtained in b) with an acid to yield a corresponding acid addition salt.

8. A pharmaceutical composition comprising a compound according to claim 1 and at least one pharmaceutically acceptable carrier or adjuvant.

9. A method of treating or inhibiting thrombosis in a patient in need thereof, said method comprising administering to said patient a therapeutically effective amount of a compound according to claim 1.

10. A method according to claim 9, wherein said thrombosis is venous thrombosis.

* * * * *